(12) United States Patent
Jiang et al.

(10) Patent No.: US 9,895,546 B2
(45) Date of Patent: Feb. 20, 2018

(54) PATIENT REMOTE AND ASSOCIATED METHODS OF USE WITH A NERVE STIMULATION SYSTEM

(71) Applicant: Axonics Modulation Technologies, Inc., Irvine, CA (US)

(72) Inventors: Guangqiang Jiang, Irvine, CA (US); John Woock, Costa Mesa, CA (US); Dennis Schroeder, Los Angeles, CA (US); Eric Schmid, Los Angeles, CA (US)

(73) Assignee: AXONICS MODULATION TECHNOLOGIES, INC., Irvine, CA (US)

( * ) Notice: Subject to any disclaimer, the term of this patent is extended or adjusted under 35 U.S.C. 154(b) by 0 days.

(21) Appl. No.: 14/992,777

(22) Filed: Jan. 11, 2016

(65) Prior Publication Data

US 2016/0199659 A1    Jul. 14, 2016

Related U.S. Application Data

(60) Provisional application No. 62/101,666, filed on Jan. 9, 2015.

(51) Int. Cl.
   *A61N 1/36* (2006.01)
   *A61N 1/372* (2006.01)

(52) U.S. Cl.
   CPC ..... *A61N 1/37247* (2013.01); *A61N 1/36057* (2013.01); *A61N 1/36128* (2013.01);
   (Continued)

(58) Field of Classification Search
   CPC .................. A61N 1/37247; A61N 1/37235
   See application file for complete search history.

(56) References Cited

U.S. PATENT DOCUMENTS

| 3,646,940 A | 3/1972 | Timm et al. |
| 4,019,518 A | 4/1977 | Maurer et al. |

(Continued)

FOREIGN PATENT DOCUMENTS

| EP | 1680182 B1 | 7/2006 |
| EP | 1904153 B1 | 4/2008 |

(Continued)

OTHER PUBLICATIONS

Bosch, J., et al., Sacral (S3) Segmental Nerve Stimulation as a Treatment for Urge Incontinence in Patients With Detrusor Instability: Results of Chronic Electrical Stimulation Using an Implantable Neural Prosthesis, The Journal of Urology, Aug. 1995, vol. 154, pp. 504-507.

(Continued)

*Primary Examiner* — George Evanisko
(74) *Attorney, Agent, or Firm* — Kilpatrick Townsend & Stockton LLP

(57) ABSTRACT

A neurostimulation system having an external or an implantable pulse generator programmed to innervate a specific nerve or group of nerves in a patient through an electrode as a mode of treatment, having a patient remote that wirelessly communicates with the pulse generator to increase stimulation, decrease stimulation, and provide indications to a patient regarding the status of the neurostimulation system. The patient remote can allow for adjustment of stimulation power within a clinically effective range and for turning on and turning off the pulse generator. The patient remote and neurostimulation system can also store a stimulation level when the pulse generator is turned off and automatically restore the pulse generator to the stored stimulation level when the pulse generator is turned on.

19 Claims, 14 Drawing Sheets

(52) U.S. Cl.
CPC ...... *A61N 1/37211* (2013.01); *A61N 1/37235* (2013.01); *A61N 1/37241* (2013.01); *A61N 1/36132* (2013.01); *A61N 1/36142* (2013.01); *A61N 1/36146* (2013.01)

(56) References Cited

U.S. PATENT DOCUMENTS

| | | | |
|---|---|---|---|
| 4,044,774 A | 8/1977 | Corbin et al. |
| 4,340,062 A | 7/1982 | Thompson et al. |
| 4,558,702 A | 12/1985 | Barreras et al. |
| 4,744,371 A | 5/1988 | Harris |
| 5,690,693 A | 11/1997 | Wang et al. |
| 5,702,428 A | 12/1997 | Tippey et al. |
| 5,702,431 A | 12/1997 | Wang et al. |
| 5,735,887 A | 4/1998 | Barreras, Sr. et al. |
| 5,741,316 A | 4/1998 | Chen et al. |
| 5,876,423 A | 3/1999 | Braun |
| 6,027,456 A | 2/2000 | Feler et al. |
| 6,035,237 A | 3/2000 | Schulman et al. |
| 6,052,624 A | 4/2000 | Mann |
| 6,055,456 A | 4/2000 | Gerber |
| 6,057,513 A | 5/2000 | Ushikoshi et al. |
| 6,067,474 A | 5/2000 | Schulman et al. |
| 6,076,017 A | 6/2000 | Taylor et al. |
| 6,172,556 B1 | 1/2001 | Prentice |
| 6,178,353 B1 | 1/2001 | Griffith et al. |
| 6,191,365 B1 | 2/2001 | Avellanet |
| 6,208,894 B1 | 3/2001 | Schulman et al. |
| 6,212,431 B1 | 4/2001 | Hahn et al. |
| 6,221,513 B1 | 4/2001 | Lasater |
| 6,246,911 B1 | 6/2001 | Seligman |
| 6,249,703 B1 | 6/2001 | Stanton et al. |
| 6,265,789 B1 | 7/2001 | Honda et al. |
| 6,306,100 B1 | 10/2001 | Prass |
| 6,315,721 B2 | 11/2001 | Schulman et al. |
| 6,354,991 B1 | 3/2002 | Gross et al. |
| 6,360,750 B1 | 3/2002 | Gerber et al. |
| 6,393,325 B1 | 5/2002 | Mann et al. |
| 6,438,423 B1 | 8/2002 | Rezai et al. |
| 6,442,434 B1 | 8/2002 | Zarinetchi et al. |
| 6,466,817 B1 | 10/2002 | Kaula et al. |
| 6,505,075 B1 | 1/2003 | Weiner |
| 6,516,227 B1 | 2/2003 | Meadows et al. |
| 6,584,355 B2 | 6/2003 | Stessman |
| 6,600,954 B2 | 7/2003 | Cohen et al. |
| 6,609,031 B1 | 8/2003 | Law et al. |
| 6,609,032 B1 | 8/2003 | Woods et al. |
| 6,652,449 B1 | 11/2003 | Gross et al. |
| 6,662,051 B1 | 12/2003 | Eraker et al. |
| 6,721,603 B2 | 4/2004 | Zabara et al. |
| 6,735,474 B1 | 5/2004 | Loeb et al. |
| 6,745,077 B1 | 6/2004 | Griffith et al. |
| 6,809,701 B2 | 10/2004 | Amundson et al. |
| 6,836,684 B1 | 12/2004 | Rijkhoff et al. |
| 6,847,849 B2 | 1/2005 | Mamo et al. |
| 6,892,098 B2 | 5/2005 | Ayal et al. |
| 6,895,280 B2 | 5/2005 | Meadows et al. |
| 6,896,651 B2 | 5/2005 | Gross et al. |
| 6,901,287 B2 | 5/2005 | Davis et al. |
| 6,941,171 B2 | 9/2005 | Mann et al. |
| 6,971,393 B1 | 12/2005 | Mamo et al. |
| 6,989,200 B2 | 1/2006 | Byers et al. |
| 6,990,376 B2 | 1/2006 | Tanagho et al. |
| 6,999,819 B2 | 2/2006 | Swoyer et al. |
| 7,043,304 B1 | 5/2006 | Griffith et al. |
| 7,051,419 B2 | 5/2006 | Schrom et al. |
| 7,054,689 B1 | 5/2006 | Whitehurst et al. |
| 7,069,081 B2 | 6/2006 | Biggs et al. |
| 7,127,298 B1 | 10/2006 | He et al. |
| 7,142,925 B1 | 11/2006 | Bhadra et al. |
| 7,146,219 B2 | 12/2006 | Sieracki et al. |
| 7,151,914 B2 | 12/2006 | Brewer |
| 7,167,749 B2 | 1/2007 | Biggs et al. |
| 7,177,690 B2 | 2/2007 | Woods et al. |
| 7,177,698 B2 | 2/2007 | Klosterman et al. |
| 7,181,286 B2 | 2/2007 | Sieracki et al. |
| 7,187,978 B2 | 3/2007 | Malek et al. |
| 7,191,005 B2 | 3/2007 | Stessman |
| 7,212,110 B1 | 5/2007 | Martin et al. |
| 7,225,032 B2 | 5/2007 | Schmeling et al. |
| 7,231,254 B2 | 6/2007 | DiLorenzo |
| 7,234,853 B2 | 6/2007 | Givoletti |
| 7,245,972 B2 | 7/2007 | Davis |
| 7,286,880 B2 | 10/2007 | Olson et al. |
| 7,305,268 B2 | 12/2007 | Gliner et al. |
| 7,317,948 B1 | 1/2008 | King et al. |
| 7,324,852 B2 | 1/2008 | Barolat et al. |
| 7,324,853 B2 | 1/2008 | Ayal et al. |
| 7,326,181 B2 | 2/2008 | Katims |
| 7,328,068 B2 | 2/2008 | Spinelli et al. |
| 7,330,764 B2 | 2/2008 | Swoyer et al. |
| 7,359,751 B1 | 4/2008 | Erickson et al. |
| 7,369,894 B2 | 5/2008 | Gerber |
| 7,386,348 B2 | 6/2008 | North et al. |
| 7,387,603 B2 | 6/2008 | Gross et al. |
| 7,396,265 B2 | 7/2008 | Darley et al. |
| 7,415,308 B2 | 8/2008 | Gerber et al. |
| 7,444,181 B2 | 10/2008 | Shi et al. |
| 7,450,991 B2 | 11/2008 | Smith et al. |
| 7,460,911 B2 | 12/2008 | Cosendai et al. |
| 7,463,928 B2 | 12/2008 | Lee et al. |
| 7,470,236 B1 | 12/2008 | Kelleher et al. |
| 7,483,752 B2 | 1/2009 | Von Arx et al. |
| 7,496,404 B2 | 2/2009 | Meadows et al. |
| 7,515,967 B2 | 4/2009 | Phillips et al. |
| 7,532,936 B2 | 5/2009 | Erickson et al. |
| 7,539,538 B2 | 5/2009 | Parramon et al. |
| 7,551,960 B2 | 6/2009 | Forsberg et al. |
| 7,555,346 B1 | 6/2009 | Woods et al. |
| 7,565,203 B2 | 7/2009 | Greenberg et al. |
| 7,578,819 B2 | 8/2009 | Bleich et al. |
| 7,580,752 B2 | 8/2009 | Gerber et al. |
| 7,582,053 B2 | 9/2009 | Gross et al. |
| 7,617,002 B2 | 11/2009 | Goetz |
| 7,640,059 B2 | 12/2009 | Forsberg et al. |
| 7,643,880 B2 | 1/2010 | Tanagho et al. |
| 7,647,117 B2 | 1/2010 | Bauhahn |
| 7,706,889 B2 | 4/2010 | Gerber et al. |
| 7,720,547 B2 | 5/2010 | Denker et al. |
| 7,725,191 B2 | 5/2010 | Greenberg et al. |
| 7,734,355 B2 | 6/2010 | Cohen et al. |
| 7,738,963 B2 | 6/2010 | Hickman et al. |
| 7,738,965 B2 | 6/2010 | Phillips et al. |
| 7,747,330 B2 | 6/2010 | Nolan et al. |
| 7,771,838 B1 | 8/2010 | He et al. |
| 7,774,069 B2 | 8/2010 | Olson et al. |
| 7,801,619 B2 | 9/2010 | Gerber et al. |
| 7,813,803 B2 | 10/2010 | Heruth et al. |
| 7,813,809 B2 | 10/2010 | Strother et al. |
| 7,826,901 B2 | 11/2010 | Lee et al. |
| 7,848,818 B2 | 12/2010 | Barolat et al. |
| 7,904,167 B2 | 3/2011 | Klosterman et al. |
| 7,912,555 B2 | 3/2011 | Swoyer et al. |
| 7,925,357 B2 | 4/2011 | Phillips et al. |
| 7,932,696 B2 | 4/2011 | Peterson |
| 7,933,656 B2 | 4/2011 | Sieracki et al. |
| 7,935,051 B2 | 5/2011 | Miles et al. |
| 7,937,158 B2 | 5/2011 | Erickson et al. |
| 7,952,349 B2 | 5/2011 | Huang et al. |
| 7,957,818 B2 | 6/2011 | Swoyer |
| 7,979,119 B2 | 7/2011 | Kothandaraman et al. |
| 7,979,126 B2 | 7/2011 | Payne et al. |
| 7,988,507 B2 | 8/2011 | Darley et al. |
| 8,000,782 B2 | 8/2011 | Gharib et al. |
| 8,000,805 B2 | 8/2011 | Swoyer et al. |
| 8,005,535 B2 | 8/2011 | Gharib et al. |
| 8,005,549 B2 | 8/2011 | Boser et al. |
| 8,005,550 B2 | 8/2011 | Boser et al. |
| 8,019,423 B2 | 9/2011 | Possover |
| 8,024,047 B2 | 9/2011 | Olson et al. |
| 8,036,756 B2 | 10/2011 | Swoyer et al. |
| 8,044,635 B2 | 10/2011 | Peterson |
| 8,050,769 B2 | 11/2011 | Gharib et al. |
| 8,055,337 B2 | 11/2011 | Moffitt et al. |

(56) References Cited

U.S. PATENT DOCUMENTS

| | | |
|---|---|---|
| 8,068,912 B2 | 11/2011 | Kaula et al. |
| 8,083,663 B2 | 12/2011 | Gross et al. |
| 8,103,360 B2 | 1/2012 | Foster |
| 8,116,862 B2 | 2/2012 | Stevenson et al. |
| 8,121,701 B2 | 2/2012 | Woods et al. |
| 8,129,942 B2 | 3/2012 | Park et al. |
| 8,131,358 B2 | 3/2012 | Moffitt et al. |
| 8,140,168 B2 | 3/2012 | Olson et al. |
| 8,145,324 B1 | 3/2012 | Stevenson et al. |
| 8,150,530 B2 | 4/2012 | Wesselink |
| 8,175,717 B2 | 5/2012 | Haller et al. |
| 8,180,451 B2 | 5/2012 | Hickman et al. |
| 8,180,452 B2 | 5/2012 | Shaquer |
| 8,180,461 B2 | 5/2012 | Mamo et al. |
| 8,214,042 B2 | 7/2012 | Ozawa et al. |
| 8,214,048 B1 | 7/2012 | Whitehurst et al. |
| 8,214,051 B2 | 7/2012 | Sieracki et al. |
| 8,219,196 B2 | 7/2012 | Torgerson |
| 8,219,202 B2 | 7/2012 | Giftakis et al. |
| 8,233,990 B2 | 7/2012 | Goetz |
| 8,255,057 B2 | 8/2012 | Fang et al. |
| 8,311,636 B2 | 11/2012 | Gerber et al. |
| 8,314,594 B2 | 11/2012 | Scott et al. |
| 8,332,040 B1 | 12/2012 | Winstrom |
| 8,340,786 B2 | 12/2012 | Gross et al. |
| 8,362,742 B2 | 1/2013 | Kallmyer |
| 8,369,943 B2 | 2/2013 | Shuros et al. |
| 8,386,048 B2 | 2/2013 | McClure et al. |
| 8,417,346 B2 | 4/2013 | Giftakis et al. |
| 8,423,146 B2 | 4/2013 | Giftakis et al. |
| 8,447,402 B1 | 5/2013 | Jiang et al. |
| 8,447,408 B2 | 5/2013 | North et al. |
| 8,457,756 B2 | 6/2013 | Rahman |
| 8,457,758 B2 | 6/2013 | Olson et al. |
| 8,480,437 B2 | 7/2013 | Dilmaghanian et al. |
| 8,494,625 B2 | 7/2013 | Hargrove |
| 8,515,545 B2 | 8/2013 | Trier |
| 8,538,530 B1 | 9/2013 | Orinski |
| 8,543,223 B2 | 9/2013 | Sage et al. |
| 8,549,015 B2 | 10/2013 | Barolat |
| 8,554,322 B2 | 10/2013 | Olson et al. |
| 8,555,894 B2 | 10/2013 | Schulman et al. |
| 8,562,539 B2 | 10/2013 | Marino |
| 8,571,677 B2 | 10/2013 | Torgerson et al. |
| 8,577,474 B2 | 11/2013 | Rahman et al. |
| 8,588,917 B2 | 11/2013 | Whitehurst et al. |
| 8,626,314 B2 | 1/2014 | Swoyer et al. |
| 8,644,933 B2 | 2/2014 | Ozawa et al. |
| 8,644,940 B2 | 2/2014 | Forsell |
| 8,655,451 B2 | 2/2014 | Klosterman et al. |
| 8,655,455 B2 | 2/2014 | Mann et al. |
| 8,700,175 B2 | 4/2014 | Fell |
| 8,706,239 B2 | 4/2014 | Bharmi et al. |
| 8,725,269 B2 | 5/2014 | Nolan et al. |
| 8,738,141 B2 | 5/2014 | Smith et al. |
| 8,738,148 B2 | 5/2014 | Olson et al. |
| 8,750,985 B2 | 6/2014 | Parramon et al. |
| 8,751,008 B2 | 6/2014 | Carlton et al. |
| 8,761,897 B2 | 6/2014 | Kaula et al. |
| 8,768,452 B2 | 7/2014 | Gerber |
| 8,774,912 B2 | 7/2014 | Gerber |
| 8,954,148 B2 | 2/2015 | Labbe et al. |
| 8,989,861 B2 | 3/2015 | Su et al. |
| 9,089,712 B2 | 7/2015 | Joshi et al. |
| 9,108,063 B2 | 8/2015 | Olson et al. |
| 2002/0068960 A1 | 6/2002 | Saberski et al. |
| 2005/0104577 A1 | 5/2005 | Matei et al. |
| 2006/0142822 A1 | 6/2006 | Tulgar |
| 2006/0206166 A1 | 9/2006 | Weiner |
| 2007/0055318 A1 | 3/2007 | Forsberg et al. |
| 2007/0265675 A1 | 11/2007 | Lund et al. |
| 2007/0270921 A1 | 11/2007 | Strother et al. |
| 2007/0293914 A1 | 12/2007 | Woods et al. |
| 2008/0077192 A1 | 3/2008 | Harry et al. |
| 2008/0183236 A1 | 7/2008 | Gerber |
| 2009/0234302 A1 | 9/2009 | Hoendervoogt et al. |
| 2010/0076254 A1 | 3/2010 | Jimenez et al. |
| 2010/0076534 A1 | 3/2010 | Mock |
| 2010/0114259 A1 | 5/2010 | Herregraven et al. |
| 2010/0222847 A1 | 9/2010 | Goetz et al. |
| 2010/0318159 A1 | 12/2010 | Aghassian et al. |
| 2011/0137378 A1 | 6/2011 | Klosterman et al. |
| 2011/0144468 A1 | 6/2011 | Boggs et al. |
| 2011/0282416 A1 | 11/2011 | Hamann et al. |
| 2011/0301667 A1 | 12/2011 | Olson et al. |
| 2012/0041512 A1 | 2/2012 | Weiner |
| 2012/0046712 A1 | 2/2012 | Woods et al. |
| 2012/0130448 A1 | 5/2012 | Woods et al. |
| 2012/0197338 A1 | 8/2012 | Su et al. |
| 2012/0215285 A1 | 8/2012 | Tahmasian et al. |
| 2012/0276854 A1 | 11/2012 | Joshi et al. |
| 2012/0276856 A1 | 11/2012 | Joshi et al. |
| 2013/0004925 A1 | 1/2013 | Labbe et al. |
| 2013/0006330 A1* | 1/2013 | Wilder ............... A61N 1/37247 607/59 |
| 2013/0006331 A1 | 1/2013 | Weisgarber et al. |
| 2013/0150925 A1 | 6/2013 | Vamos et al. |
| 2013/0184773 A1 | 7/2013 | Libbus et al. |
| 2013/0197608 A1 | 8/2013 | Eiger |
| 2013/0207863 A1 | 8/2013 | Joshi |
| 2013/0261692 A1 | 10/2013 | Cardinal et al. |
| 2013/0310894 A1 | 11/2013 | Trier |
| 2013/0331909 A1 | 12/2013 | Gerber |
| 2013/0345777 A1 | 12/2013 | Feldman et al. |
| 2014/0222112 A1 | 8/2014 | Fell |
| 2014/0237806 A1 | 8/2014 | Smith et al. |
| 2014/0277270 A1 | 9/2014 | Parramon et al. |
| 2015/0065047 A1 | 3/2015 | Wu et al. |
| 2015/0214604 A1 | 7/2015 | Zhao et al. |

FOREIGN PATENT DOCUMENTS

| | | |
|---|---|---|
| EP | 2243509 A1 | 10/2010 |
| GB | 1470432 A | 4/1977 |
| WO | WO 00/56677 A1 | 3/2000 |
| WO | WO 2008/021524 A2 | 2/2008 |
| WO | 2009137683 A2 | 11/2009 |
| WO | 2010111321 A2 | 9/2010 |
| WO | WO 2011/059565 A1 | 5/2011 |

OTHER PUBLICATIONS

Ghovanloo, M., et al., A Small Size Large Voltage Compliance Programmable Current Source for Biomedical Implantable Microstimulators, Proceedings of the 25th Annual International Conference of the IEEE EMBS, Sep. 17-21, 2003, pp. 1979-1982.
Tanagho, E., et al., Bladder Pacemaker: Scientific Basis and Clinical Future, Urology, Dec. 1982, vol. 20, No. 6, pp. 614-619.
U.S. Appl. No. 62/101,888, filed Jan. 9, 2015.
U.S. Appl. No. 62/101,899, filed Jan. 9, 2015.
U.S. Appl. No. 62/041,611, filed Aug. 25, 2014.
U.S. Appl. No. 62/038,131, filed Aug. 15, 2014.
U.S. Appl. No. 62/101,897, filed Jan. 9, 2015.
U.S. Appl. No. 62/038,122, filed Aug. 15, 2014.
U.S. Appl. No. 62/101,666, filed Jan. 9, 2015.
U.S. Appl. No. 62/101,884, filed Jan. 9, 2015.
U.S. Appl. No. 62/101,782, filed Jan. 9, 2015.

* cited by examiner

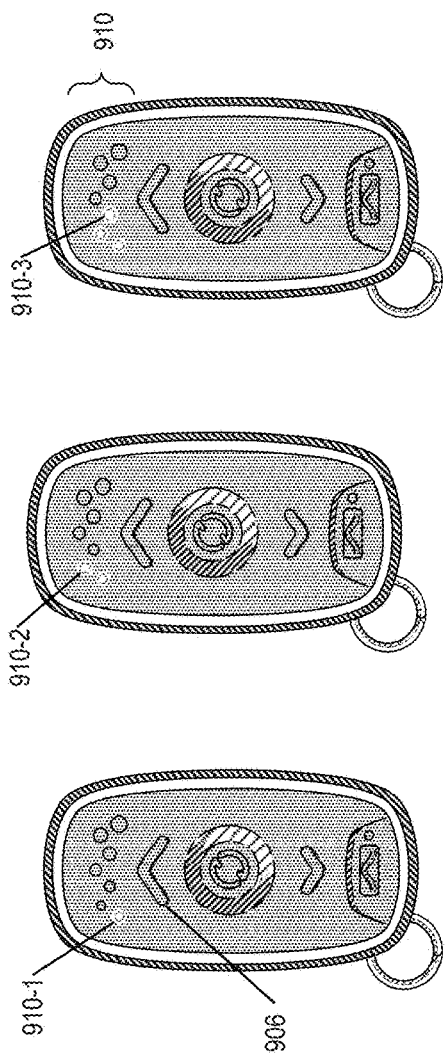
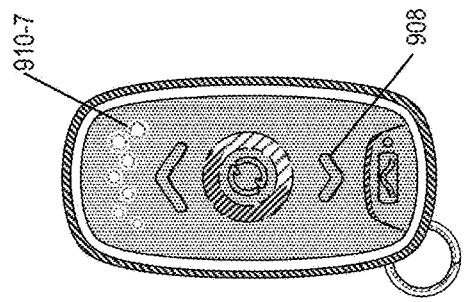
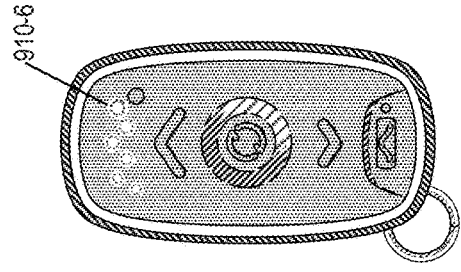
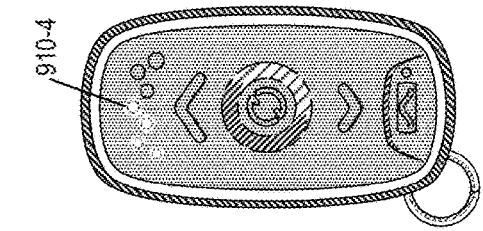

PATIENT REMOTE AND ASSOCIATED METHODS OF USE WITH A NERVE STIMULATION SYSTEM

CROSS-REFERENCES TO RELATED APPLICATIONS

The present application claims the benefit of priority to U.S. Provisional Patent Application No. 62/101,666, filed on Jan. 9, 2015, entitled "Patient Remote And Associated Methods Of Use With A Nerve Stimulation System," which is herein incorporated by reference in its entirety for all purposes.

The present application is related to U.S. Provisional Patent Application Nos. 62/038,122 filed on Aug. 15, 2014 and entitled "Devices and Methods for Anchoring of Neurostimulation Leads"; 62/038,131, filed on Aug. 15, 2014 and entitled "External Pulse Generator Device and Associated Methods for Trial Nerve Stimulation"; 62/041,611, filed on Aug. 25, 2014 and entitled "Electromyographic Lead Positioning and Stimulation Titration in a Nerve Stimulation System for Treatment of Overactive Bladder, Pain and Other Indicators"; and concurrently filed U.S. Provisional Patent Application Nos. 62/101,888, entitled "Electromyographic Lead Positioning and Stimulation Titration in a Nerve Stimulation System for Treatment of Overactive Bladder;" 62/101,899, entitled "Integrated Electromyographic Clinician Programmer For Use With an Implantable Neurostimulator;" 62/101,897, entitled "Systems and Methods for Neurostimulation Electrode Configurations Based on Neural Localization;" 62/101,884, entitled "Attachment Devices and Associated Methods of Use With a Nerve Stimulation Charging Device;" and 62/101,782, entitled "Improved Antenna and Methods of Use For an Implantable Nerve Stimulator;" each of which is assigned to the same assignee and incorporated herein by reference in its entirety for all purposes.

FIELD OF THE INVENTION

The present invention relates to neurostimulation treatment systems and associated devices, as well as methods of treatment, implantation and configuration of such treatment systems.

BACKGROUND OF THE INVENTION

Treatments with implantable neurostimulation systems have become increasingly common in recent years. While such systems have shown promise in treating a number of conditions, effectiveness of treatment may vary considerably between patients. A number of factors may lead to the very different outcomes that patients experience, and viability of treatment can be difficult to determine before implantation. For example, stimulation systems often make use of an array of electrodes to treat one or more target nerve structures. The electrodes are often mounted together on a multi-electrode lead, and the lead implanted in tissue of the patient at a position that is intended to result in electrical coupling of the electrode to the target nerve structure, typically with at least a portion of the coupling being provided via intermediate tissues. Other approaches may also be employed, for example, with one or more electrodes attached to the skin overlying the target nerve structures, implanted in cuffs around a target nerve, or the like. Regardless, the physician will typically seek to establish an appropriate treatment protocol by varying the electrical stimulation that is applied to the electrodes.

Current stimulation electrode placement/implantation techniques and known treatment setting techniques suffer from significant disadvantages. The nerve tissue structures of different patients can be quite different, with the locations and branching of nerves that perform specific functions and/or enervate specific organs being challenging to accurately predict or identify. The electrical properties of the tissue structures surrounding a target nerve structure may also be quite different among different patients, and the neural response to stimulation may be markedly dissimilar, with an electrical stimulation pulse pattern, frequency, and/or voltage that is effective to affect a body function for one patent potentially may impose significant pain on, or have limited effect for, another patient. Even in patients where implantation of a neurostimulation system provides effective treatment, frequent adjustments and changes to the stimulation protocol are often required before a suitable treatment program can be determined, often involving repeated office visits and significant discomfort for the patient before efficacy is achieved. While a number of complex and sophisticated lead structures and stimulation setting protocols have been implemented to seek to overcome these challenges, the variability in lead placement results, the clinician time to establish suitable stimulation signals, and the discomfort (and in cases the significant pain) that is imposed on the patient remain less than ideal. In addition, the lifetime and battery life of such devices is relatively short, such that implanted systems are routinely replaced every few years, which requires additional surgeries, patient discomfort, and significant costs to healthcare systems.

Furthermore, not all adjustments to neural stimulation systems have been implemented by clinicians. Patient devices can adjust stimulation or to turn off the neurostimulation system. Unfortunately, the wide variety of adjustments that can be made have the potential to confuse patients and/or eventually result in a significant reduction in long-term efficacy of these systems.

The tremendous benefits of these neural stimulation therapies have not yet been realized. Therefore, it is desirable to provide improved neurostimulation methods, systems and devices, as well as methods for implanting and configuring such neurostimulation systems for a particular patient or condition being treated. It would be particularly helpful to provide such systems and methods so as to improve ease of use by the physician in implanting and configuring the system, as well as to improve patient comfort and alleviation of symptoms for the patient. It would also be helpful to provide systems and methods to allow the patient to adjust the stimulation level delivered by such neurostimulation systems, where such adjustment is simple, unambiguous, and sufficiently limited to ensure the stimulation can remain within a clinically effective range.

BRIEF SUMMARY OF THE INVENTION

A patient remote is provided to allow a patient to adjust the stimulation level of a neurostimulation system, which can include an electrical pulse generator coupled to an implanted electrical lead. The degree of adjustment permitted to the patient through the patient remote can be limited, such that while the patient can incrementally increase or decrease the therapy delivered by the neurostimulation system, so that the level of stimulation therapy by the neurostimulation system is maintained within a clinically effective range. By providing a controlled and limited range of adjustment to a patient through the patient remote, the patient is given a straightforward and simple tool for operation of the neurostimulation system, without presenting a selection of therapy or operational programs that may unnecessarily confuse a patient or take the neurostimulation system outside of the clinically effective range. The clinically effective range of the neurostimulation system can be determined by a physician or the clinician programmer when setting the parameters of the neurostimulation system. The patient remote can also allow a patient to turn off the neurostimulation system, which may be desirable for the patient when performing activities that may inadvertently interfere with, or be inadvertently interfered by, the neurostimulation system and the nerves stimulated by the neurostimulation system.

In some embodiments a patient remote according to the present disclosure is configured to wirelessly control a nerve-stimulating pulse generator coupled to an implantable lead in a patient, where the patient remote includes: a portable housing configured to be operable in a single hand of an operator. Circuitry may be at least partially disposed within the portable housing, and an activation switch can be on an exterior surface of the portable housing and coupled with the circuitry to reconfigure or transition the patient remote between an awake mode and an asleep mode. A stimulation-increase switch can be disposed on the exterior surface of the portable housing and coupled to the circuitry so as to wirelessly increase a stimulation level of the pulse generator when the patient remote is in the awake mode. Actuation of the stimulation-increase switch for a first period of time may increase the stimulation level (including by turn stimulation on stimulation if the pulse generator was previously off). Actuation of the stimulation-increase switch for a second period of time may restore the stimulation level of the pulse generator to a previously stored or last stored stimulation level (and may also turn stimulation on). The first period of time and the second period of time can be demarked by a threshold time. In some aspects, actuation of the stimulation-increase switch for the second period of time ramps the stimulation level to the previously stored or last stored stimulation level. As described in any of the embodiments herein, previously stored stimulation level can refer to a last stored stimulation level.

In other aspects, the patient remote can further include a stimulation-decrease switch disposed on the exterior surface of the portable housing configured to wirelessly decrease the stimulation level of the pulse generator, where when the activation switch of the patient remote is in the awake mode, actuation of the stimulation-decrease switch for the first period of time decreases the stimulation level or turns off stimulation of the pulse generator, and where actuation of the stimulation-decrease switch for the second period of time stores the stimulation level in a memory element and turns off the stimulation by the pulse generator. In further aspects, actuation of the stimulation-increase switch incrementally increases the stimulation level up to three or four stimulation levels above a baseline or nominal stimulation level and actuation of the stimulation-decrease switch incrementally decreases the stimulation level down respectively to three or two stimulation levels below the baseline stimulation level. As described herein, a baseline or nominal stimulation level can be the optimum stimulation level, which can be determined by the CP or can be set by the clinician. In some aspects, this nominal stimulation level can be determined based on sensory or motor responses, qualitative sensory feedback or various combinations thereof. In some embodiments, determination of the nominal stimulation level can be based in part on a threshold level of the selected electrodes and a maximum stimulation level based on patient comfort. In some embodiments, the nominal stimulation can be determined so that incremental adjustment of stimulation levels by the patient in either direction remains within a clinically effective range. In some aspects, each stimulation level increase or stimulation level decrease of the pulse generator comprises more than five percent (5%), optionally at least ten percent (10%) of a nominal stimulation level or a current stimulation level.

In many embodiments, the patient remote can further include a stimulation-level display disposed on the exterior surface of the portable housing. The patient remote may be configured to wirelessly communicate with the pulse generator and the stimulation-level display may be configured to indicate a current stimulation level of the pulse generator when the activation switch of the patient remote is switched from the asleep mode to the awake mode. In some aspects, the stimulation-level display can include a plurality of light emitting diodes, where a number of illuminated light emitting diodes indicates the current stimulation level of the pulse generator. In other aspects, the stimulation-level display can include at least seven light emitting diodes of at least two, three or four sizes, where a baseline stimulation level can be indicated by illumination of (for example) the first three or four light emitting diodes.

In further aspects, the patient remote can also include a therapy-remaining display disposed on the exterior surface of the portable housing, and can be configured to indicate therapy remaining status based on at least a charge or voltage remaining in a battery of the pulse generator and stimulation use parameters by the patient. In such aspects, the therapy-remaining display can include a light emitting diode having at least two contrasting colors or a single color with flashing and non-flashing modes or both to indicate if the pulse generator needs re-charging, is charging, or has sufficient charge for at least four days of nominal stimulation. In particular aspects, the therapy-remaining display light emitting diode can illuminate with a non-flashing green color to indicate at least four (4) days of therapy remaining, can illuminate with a non-flashing amber color to indicate two to four (2-4) days of therapy remaining, and can illuminate with a flashing amber color to indicate less than two (2) days of therapy remaining. In some aspects, the patient remote can further include an automatic fault condition indicator disposed on the exterior surface of the portable housing that is configured to provide an alert if the pulse generator is in a fault condition. In other aspects, the patient remote can further include a haptic indicator coupled to the portable housing that is configured to vibrate when a command from the patient remote has been executed by the pulse generator. In further aspects, the nerve-stimulating pulse generator can include an external or implantable pulse generator, and the implantable lead comprises at least one electrode configured for insertion into a foramen of a sacrum near a sacral nerve.

In other embodiments, a patient remote is configured to wirelessly control a nerve-stimulating pulse generator coupled to an implantable lead, the patient remote having: a portable housing configured to be operable in a single hand of an operator and circuitry at least partially disposed within the housing; an activation switch disposed within a recessed area of the portable housing so as to allow reconfiguration or transition between an awake mode and an asleep mode; a stimulation-increase switch disposed on an exterior surface of the portable housing, configured to wirelessly increase a stimulation level of the pulse generator; and a stimulation-decrease switch disposed on the exterior surface of the portable housing, configured to wirelessly decrease a stimulation level of the pulse generator; where when the recessed activation switch of the patient remote is in the asleep mode, the stimulation-increase switch and the stimulation-decrease switch are inactivated, and where when the recessed activation switch of the patient remote is in the awake mode, the patient remote is configured to wirelessly communicate with the pulse generator. In some aspects, the stimulation-increase switch and the stimulation-decrease switch are each disposed on a raised region of the exterior surface of the portable housing, where the stimulation-increase switch can further have a tactile feature that is larger in size than that of the stimulation-decrease switch. In other aspects, actuation of the stimulation-increase switch can incrementally increase the stimulation level up to three or four stimulation levels above a baseline stimulation level, and actuation of the stimulation-decrease switch can incrementally decrease the stimulation level down respectively to three or two stimulation levels below the baseline stimulation level. In further aspects, each stimulation level increase or stimulation level decrease of the pulse generator can be at least ten percent of a baseline stimulation level or a current stimulation level.

In some embodiments, the patient remote can further include a stimulation-level display disposed on the exterior surface of the portable housing, where the patient remote is configured to wirelessly communicate with the pulse generator and the stimulation-level display is configured to indicate a current stimulation level of the pulse generator, when the activation switch of the patient remote is switched from the asleep mode to the awake mode. In some aspects, the stimulation-level display can include a plurality of light emitting diodes, where a number of illuminated light emitting diodes indicates the current stimulation level of the pulse generator. In particular aspects, the stimulation-level display can include at least seven light emitting diodes of at least three or four sizes, where a baseline stimulation level can be indicated illumination of the first three or four light emitting diodes. In other aspects, the patient remote can further include a therapy-remaining display disposed on the exterior surface of the portable housing configured to indicate therapy remaining based on at least a charge of voltage remaining in a batter of the pulse generator a stimulation use parameters by the patient. In further aspects, the therapy-remaining display can include a light emitting diode having at least two contrasting colors or a single color with flashing and non-flashing modes to indicate if the pulse generator needs re-charging, is charging, or has sufficient charge for at least four days of nominal stimulation. In such aspects, the therapy-remaining display light emitting diode can illuminate with a non-flashing green color to indicate at least four (4) days of therapy remaining, can illuminate with a non-flashing amber color to indicate two to four (2-4) days of therapy remaining, and can illuminate with a flashing amber color to indicate less than two (2) days of therapy remaining. In some aspects, the patient remote can further have an automatic fault condition indicator disposed on the exterior surface of the portable housing configured to provide an alert if the pulse generator is in a fault condition. In other aspects, the patient remote can further have a haptic indicator coupled to the portable housing configured to vibrate when a command from the patient remote has been executed by the pulse generator.

In further embodiments, the present disclosure is directed to a method for controlling a nerve-stimulating pulse generator coupled to an implantable lead within a patient with a patient remote, the method including: wirelessly communicating with the pulse generator after an activation switch of the patient remote reconfigures or transitions the patient remote from an asleep mode to an awake mode; displaying a current stimulation setting of the pulse generator on a stimulation-level display of the patient remote; and wirelessly increasing a stimulation level or turning on stimulation of the pulse generator when a stimulation-increase switch of the patient remote is actuated for a first period of time or turning on and restoring stimulation of the pulse generator to a previously stored stimulation level when the stimulation-increase switch of the patient remote is actuated for a second period of time. In some aspects, the method can include wirelessly decreasing the stimulation level or turning off stimulation of the pulse generator when a stimulation-decrease switch of the patient remote is actuated for the first period of time or storing the stimulation level and turning off stimulation of the pulse generator when the stimulation-decrease switch of the patient remote is actuated for the second period of time. In other aspects, the method can further include automatically switching the patient remote from the awake mode to the asleep mode after a period of patient remote inactivity, wherein the period of inactivity comprises at least ten (10) seconds. In further aspects, the method can also include deactivating the stimulation-increase switch and stimulation-decrease switch of the patient remote when the activation switch of the patient remote is in the asleep mode. In yet further aspects, the method can include displaying a status of therapy remaining in the pulse generator on the patient remote, where the therapy remaining status is based on at least a charge or voltage remaining in a battery of the pulse generator and stimulation use parameters by the patient.

In some embodiments, the present disclosure is directed to a method for controlling a nerve-stimulating pulse generator coupled to an implantable lead within a patient with a patient remote, the method at least including actuating an activation switch to switch a patient remote between an awake mode and an asleep mode, where when the patient remote in the awake mode: actuating a stimulation-increase switch for a first period of time to turn on or incrementally increase the stimulation level of the pulse generator or actuating the stimulation-increase switch for a second period of time to turning on and restoring stimulation of the pulse generator to a previously stored stimulation level; and actuating a stimulation-decrease switch for the first period of time to turn off or incrementally decrease the stimulation level of the pulse generator or actuating the stimulation-decrease switch for the second period of time to store the current stimulation level and turn off stimulation of the pulse generator.

In other embodiments, the present disclosure is directed to an implantable nerve stimulation system having an implantable neurostimulator and a portable patient remote configured to wirelessly control the implantable neurostimulator, where the portable patient remote can include: an external housing having an oblong or rectangular shape; a stimulation-increase switch disposed on an exterior surface of the portable housing configured to wirelessly increase a stimulation level of the implantable neurostimulator; a stimulation-decrease switch disposed on the exterior surface of the portable housing configured to wirelessly decrease a stimulation level of the implantable neurostimulator; and a recessed activation switch disposed on the external housing and having an awake mode and an asleep mode, where when the recessed activation switch of the patient remote is in the asleep mode, the stimulation-increase switch and the stimulation-decrease switch are inactivated, and where when the recessed activation switch of the patient remote is in the awake mode, the patient remote is configured to wirelessly communicate with the implantable neurostimulator and actuation of the stimulation-increase switch for a first period of time increases the stimulation level or turns on stimulation of the implantable neurostimulator while actuation of the stimulation-increase switch for a second period of time turns on stimulation of the implantable neurostimulator and restores the stimulation level of the implantable neurostimulator to a previously stored stimulation level.

In further embodiments, the present disclosure is directed to a system for treating a patient with a disorder associated with a nerve, where the system includes a nerve-stimulating pulse generator having wireless communication circuitry and a plurality of stimulation levels; an implantable lead configured to be coupled with the pulse generator and implanted in the patient in operative communication with the nerve; and a patient remote. In such embodiments, the patent remote can include: a portable housing configured to be carried daily by the patient; circuitry disposed within the portable housing, the circuitry configured to wirelessly communicate with the wireless communication circuitry of the pulse generator; and a stimulation level varying switch disposed on the portable housing, the stimulation level switch coupled to the circuitry so as to wirelessly alter an applied stimulation level of the pulse generator when the switch is actuated, the applied stimulation level being selected from among the plurality of stimulation levels of the pulse generator so that actuation of the stimulation level switch allows the patient to select a level of stimulation being applied by the pulse generator to the lead; where the patient remote and pulse generator are configured so that the plurality of stimulation levels selectable by the patient using the patient remote define a monovariant range of stimulation levels extending from a least selectable stimulation level to a greatest selectable stimulation level.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

FIGS. 9-1 to 9-7 are schematic illustrations of a patient remote showing a progression of stimulation levels, in accordance with aspects of the invention.

FIGS. 9-8 and 9-9 are schematic illustrations of a patient remote with a therapy-remaining display showing levels of therapy remaining for a neurostimulation system, in accordance with aspects of the invention.

FIG. 9-10 is a schematic illustration of a patient remote with an illuminated fault condition indicator, in accordance with aspects of the invention.

FIG. 10 is a functional block diagram of components of a patient remote, in accordance with aspects of the invention.

DETAILED DESCRIPTION OF THE INVENTION

Figure 1:
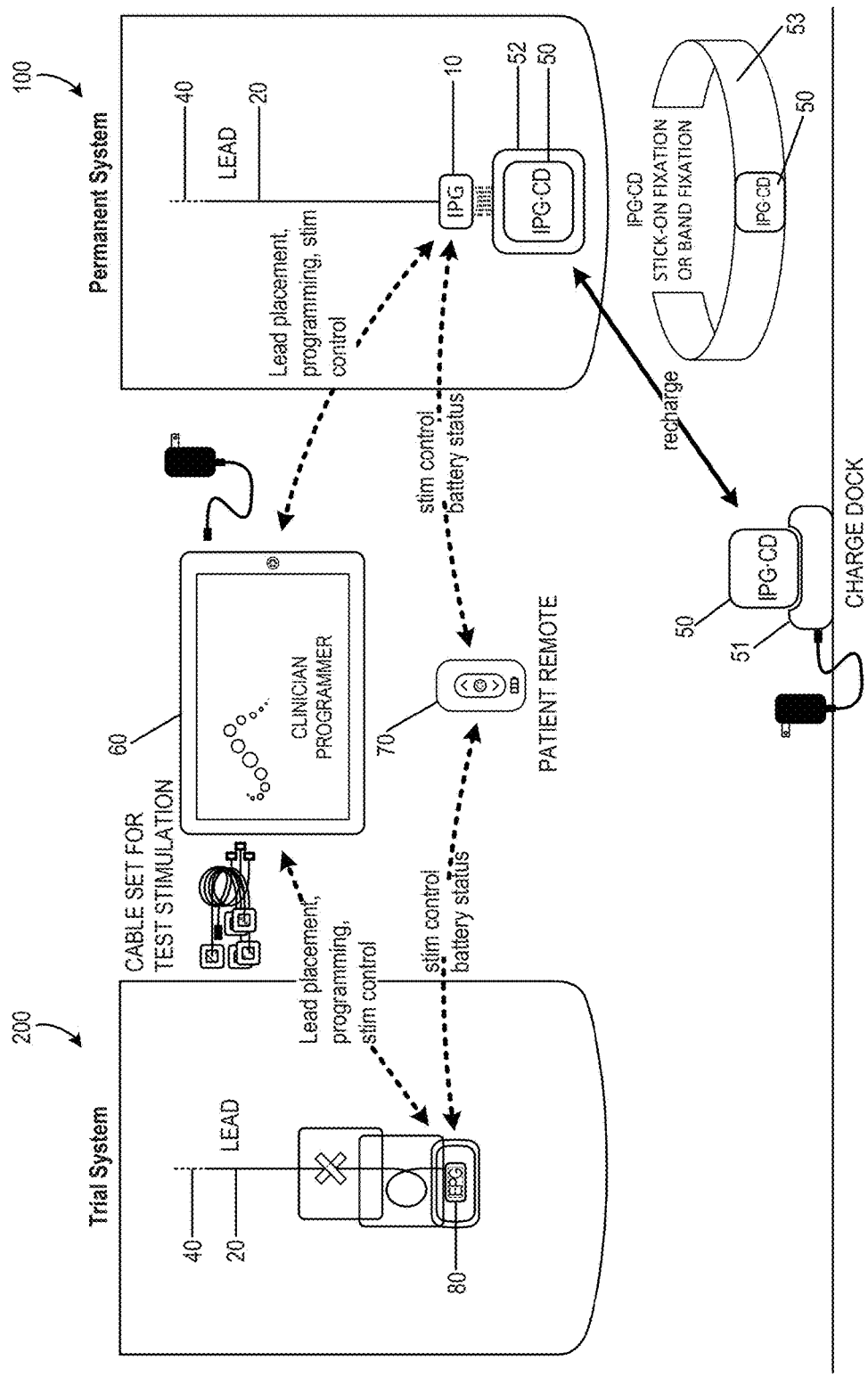
FIG. 1 schematically illustrates a nerve stimulation system, which includes a clinician programmer and a patient remote used in positioning and/or programming of both a trial neurostimulation system and a permanently implanted neurostimulation system, in accordance with aspects of the invention.

The present invention relates to neurostimulation treatment systems and associated devices, as well as methods of treatment, implantation/placement and configuration of such treatment systems. In one particular embodiment, the invention relates to sacral nerve stimulation treatment systems configured to treat overactive bladder ("OAB") and relieve symptoms of bladder related dysfunction. In addition, the descriptions herein may also be used to treat other forms of urinary dysfunction and to treat fecal dysfunction, therefore, throughout the description it should be understood that what is described for OAB applies equally to other forms of urinary dysfunction and fecal dysfunction. It will be appreciated however that the present invention may also be utilized for the treatment of pain or other indications, such as movement or affective disorders, as will be appreciated by one of skill in the art.

I. Neurostimulation Indications

Neurostimulation (or neuromodulation as may be used interchangeably hereunder) treatment systems, such as any of those described herein, can be used to treat a variety of ailments and associated symptoms, such as acute pain disorders, movement disorders, affective disorders, as well as bladder related dysfunction. Examples of pain disorders that may be treated by neurostimulation include failed back surgery syndrome, reflex sympathetic dystrophy or complex regional pain syndrome, causalgia, arachnoiditis, and peripheral neuropathy. Movement orders include muscle paralysis, tremor, dystonia and Parkinson's disease. Affective disorders include depressions, obsessive-compulsive disorder, cluster headache, Tourette syndrome and certain types of chronic pain. Bladder related dysfunctions include but are not limited to OAB, urge incontinence, urgency-frequency, and urinary retention. OAB can include urge incontinence and urgency-frequency alone or in combination. Urge incontinence is the involuntary loss or urine associated with a sudden, strong desire to void (urgency). Urgency-frequency is the frequent, often uncontrollable urges to urinate (urgency) that often result in voiding in very small amounts (frequency). Urinary retention is the inability to empty the bladder. Neurostimulation treatments can be configured to address a particular condition by effecting neurostimulation of targeted nerve tissues relating to the sensory and/or motor control associated with that condition or associated symptom.

In one aspect, the methods and systems described herein are particularly suited for treatment of urinary and fecal dysfunctions. These conditions have been historically under-recognized and significantly underserved by the medical community. OAB is one of the most common urinary dysfunctions. It is a complex condition characterized by the presence of bothersome urinary symptoms, including urgency, frequency, nocturia and urge incontinence. It is estimated that about 33 million Americans suffer from OAB. Of the adult population, about 30% of all men and 40% of all women live with OAB symptoms.

OAB symptoms can have a significant negative impact on the psychosocial functioning and the quality of life of patients. People with OAB often restrict activities and/or develop coping strategies. Furthermore, OAB imposes a significant financial burden on individuals, their families, and healthcare organizations. The prevalence of co-morbid conditions is also significantly higher for patients with OAB than in the general population. Co-morbidities may include falls and fractures, urinary tract infections, skin infections, vulvovaginitis, cardiovascular, and central nervous system pathologies. Chronic constipation, fecal incontinence, and overlapping chronic constipation occur more frequently in patients with OAB.

Conventional treatments of OAB generally include lifestyle modifications as a first course of action. Lifestyle modifications include eliminating bladder irritants (such as caffeine) from the diet, managing fluid intake, reducing weight, stopping smoking, and managing bowel regularity. Behavioral modifications include changing voiding habits (such as bladder training and delayed voiding), training pelvic floor muscles to improve strength and control of urethral sphincter, biofeedback and techniques for urge suppression. Medications are considered a second-line treatment for OAB. These include anti-cholinergic medications (oral, transdermal patch, and gel) and oral beta-3 adrenergic agonists. However, anti-cholinergics are frequently associated with bothersome, systemic side effects including dry mouth, constipation, urinary retention, blurred vision, somnolence, and confusion. Studies have found that more than 50% of patients stop using anti-cholinergic medications within 90 days due to a lack of benefit, adverse events, or cost.

When these approaches are unsuccessful, third-line treatment options suggested by the American Urological Association include intradetrusor (bladder smooth muscle) injections of Botulinum Toxin (BoNT-A), Percutaneous Tibial Nerve Stimulation (PTNS) and Sacral Nerve Stimulation (SNM). BoNT-A (Botox®) is administered via a series of intradetrusor injections under cystoscopic guidance, but repeat injections of Botox are generally required every 4 to 12 months to maintain effect and Botox may undesirably result in urinary retention. A number or randomized controlled studies have shown some efficacy of BoNT-A in OAB patients, but long-term safety and effectiveness of BoNT-A for OAB is largely unknown.

Alternative treatment methods, typically considered when the above approaches prove ineffective, is neurostimulation of nerves relating to the urinary system. Such neurostimulation methods include PTNS and SNM. PTNS therapy consists of weekly, 30-minute sessions over a period of 12 weeks, each session using electrical stimulation that is delivered from a hand-held stimulator to the sacral plexus via the tibial nerve. For patients who respond well and continue treatment, ongoing sessions, typically every 3-4 weeks, are needed to maintain symptom reduction. There is potential for declining efficacy if patients fail to adhere to the treatment schedule. Efficacy of PTNS has been demonstrated in a few randomized-controlled studies, however, long-term safety and effectiveness of PTNS is relatively unknown at this time.

II. Sacral Neuromodulation

SNM is an established therapy that provides a safe, effective, reversible, and long-lasting treatment option for the management of urge incontinence, urgency-frequency, and non-obstructive urinary retention. SNM therapy involves the use of mild electrical pulses to stimulate the sacral nerves located in the lower back. Electrodes are placed next to a sacral nerve, usually at the S3 level, by inserting the electrode leads into the corresponding foramen of the sacrum. The electrodes are inserted subcutaneously and are subsequently attached to an implantable pulse generator (IPG). The safety and effectiveness of SNM for the treatment of OAB, including durability at five years for both urge incontinence and urgency-frequency patients, is supported by multiple studies and is well-documented. SNM has also been approved to treat chronic fecal incontinence in patients who have failed or are not candidates for more conservative treatments.

A. Implantation of Sacral Neuromodulation System

Currently, SNM qualification has a trial phase, and is followed if successful by a permanent implant. The trial phase is a test stimulation period where the patient is allowed to evaluate whether the therapy is effective. Typically, there are two techniques that are utilized to perform the test stimulation. The first is an office-based procedure termed the Percutaneous Nerve Evaluation (PNE) and the other is a staged trial.

In the PNE, a foramen needle is typically used first to identify the optimal stimulation location, usually at the S3 level, and to evaluate the integrity of the sacral nerves. Motor and sensory responses are used to verify correct needle placement, as described in Table 1 below. A temporary stimulation lead (a unipolar electrode) is then placed near the sacral nerve under local anesthesia. This procedure can be performed in an office setting without fluoroscopy. The temporary lead is then connected to an external pulse generator (EPG) taped onto the skin of the patient during the trial phase. The stimulation level can be adjusted to provide an optimal comfort level for the particular patient. The patient will monitor his or her voiding for 3 to 7 days to see if there is any symptom improvement. The advantage of the PNE is that it is an incision free procedure that can be performed in the physician's office using local anesthesia. The disadvantage is that the temporary lead is not securely anchored in place and has the propensity to migrate away from the nerve with physical activity and thereby cause failure of the therapy. If a patient fails this trial test, the physician may still recommend the staged trial as described below. If the PNE trial is positive, the temporary trial lead is removed and a permanent quadri-polar tined lead is implanted along with an IPG under general anesthesia.

Other neuromodulation applications may have any number of electrodes and more than one lead as the therapy may require.

Figure 3A:
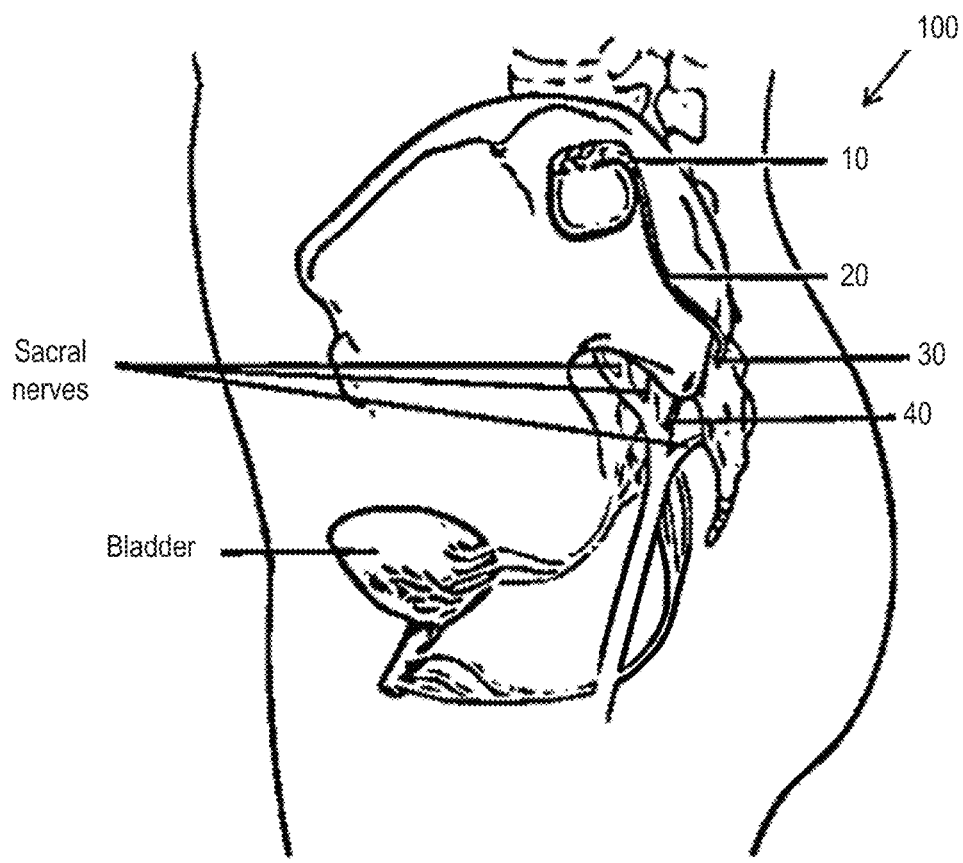
FIG. 3A shows an example of a fully implanted neurostimulation system in accordance with aspects of the invention.

A staged trial involves the implantation of the permanent quadri-polar tined stimulation lead into the patient from the start. It also requires the use of a foramen needle to identify the nerve and optimal stimulation location. The lead is implanted near the S3 sacral nerve and is connected to an EPG via a lead extension. This procedure is performed under fluoroscopic guidance in an operating room and under local or general anesthesia. The EPG is adjusted to provide an optimal comfort level for the patient and the patient monitors his or her voiding for up to two weeks. If the patient obtains meaningful symptom improvement, he or she is considered a suitable candidate for permanent implantation of the IPG under general anesthesia, typically in the upper buttock area, as shown in FIGS. 1 and 3A.

patients with urinary retention so normal voiding can be facilitated. In patients with fecal incontinence, it is hypothesized that SNM stimulates pudendal afferent somatic fibers that inhibit colonic propulsive activity and activates the internal anal sphincter, which in turn improves the symptoms of fecal incontinence patients. The present invention relates to a system adapted to deliver neurostimulation to targeted nerve tissues in a manner that disrupt, inhibit, or prevent neural activity in the targeted nerve tissues so as to provide therapeutic effect in treatment of OAB or bladder related dysfunction. In one aspect, the system is adapted to provide therapeutic effect by neurostimulation without inducing motor control of the muscles associated with OAB or bladder related dysfunction by the delivered neurostimulation. In another aspect, the system is adapted to provide such therapeutic effect by delivery of sub-threshold neurostimulation below a threshold that induces paresthesia and/

TABLE 1

Motor and Sensory Responses of SNM at Different Sacral Nerve Roots

| Nerve Innervation | Response | | |
|---|---|---|---|
| | Pelvic Floor | Foot/calf/leg | Sensation |
| S2 -Primary somatic contributor of pudendal nerve for external sphincter, leg, foot | "Clamp" * of anal sphincter | Leg/hip rotation, plantar flexion of entire foot, contraction of calf | Contraction of base of penis, vagina |
| S3 - Virtually all pelvic autonomic functions and striated mucle (levetor ani) | "bellows" ** of perineum | Plantar flexion of great toe, occasionally other toes | Pulling in rectum, extending forward to scrotum or labia |
| S4 - Pelvic autonomic and somatic; No leg pr foot | "bellows" ** | No lower extremity motor stimulation | Pulling in rectum only |

In regard to measuring outcomes for SNM treatment of voiding dysfunction, the voiding dysfunction indications (e.g., urge incontinence, urgency-frequency, and non-obstructive urinary retention) are evaluated by unique primary voiding diary variables. The therapy outcomes are measured using these same variables. SNM therapy is considered successful if a minimum of 50% improvement occurs in any of primary voiding diary variables compared with the baseline. For urge incontinence patients, these voiding diary variables may include: number of leaking episodes per day, number of heavy leaking episodes per day, and number of pads used per day. For patients with urgency-frequency, primary voiding diary variables may include: number of voids per day, volume voided per void and degree of urgency experienced before each void. For patients with retention, primary voiding diary variables may include: catheterized volume per catheterization and number of catheterizations per day.

The mechanism of action of SNM is multifactorial and impacts the neuro-axis at several different levels. In patients with OAB, it is believed that pudendal afferents can activate the inhibitory reflexes that promote bladder storage by inhibiting the afferent limb of an abnormal voiding reflex. This blocks input to the pontine micturition center, thereby restricting involuntary detrusor contractions without interfering with normal voiding patterns. For patients with urinary retention, SNM is believed to activate the pudendal nerve afferents originating from the pelvic organs into the spinal cord. At the level of the spinal cord, pudendal afferents may turn on voiding reflexes by suppressing exaggerated guarding reflexes, thus relieving symptoms of or neuromuscular response or to allow adjustment of neurostimulation to delivery therapy at sub-threshold levels.

B. Positioning Neurostimulation Leads with EMG

While conventional approaches have shown efficacy in treatment of bladder related dysfunction, there exists a need to improve positioning of the neurostimulation leads and consistency between the trial and permanent implantation positions of the lead.

Neurostimulation relies on consistently delivering therapeutic stimulation from a pulse generator, via one or more neurostimulation electrodes, to particular nerves or targeted regions. The neurostimulation electrodes are provided on a distal end of an implantable lead that can be advanced through a tunnel formed in patient tissue. Implantable neurostimulation systems provide patients with great freedom and mobility, but it may be easier to adjust the neurostimulation electrodes of such systems before they are surgically implanted. It is desirable for the physician to confirm that the patient has desired motor and/or sensory responses before implanting an IPG. For at least some treatments (including treatments of at least some forms of urinary and/or fecal dysfunction), demonstrating appropriate motor responses may be highly beneficial for accurate and objective lead placement while the sensory response may not be required or not available (e.g., patient is under general anesthesia).

Placement and calibration of the neurostimulation electrodes and implantable leads sufficiently close to specific nerves can be beneficial for the efficacy of treatment. Accordingly, aspects and embodiments of the present disclosure are directed to aiding and refining the accuracy and precision of neurostimulation electrode placement. Further, aspects and embodiments of the present disclosure are directed to aiding and refining protocols for setting therapeutic treatment signal parameters for a stimulation program implemented through implanted neurostimulation electrodes.

Prior to implantation of the permanent device, patients may undergo an initial testing phase to estimate potential response to treatment. As discussed above, PNE may be done under local anesthesia, using a test needle to identify the appropriate sacral nerve(s) according to a subjective sensory response by the patient. Other testing procedures can involve a two-stage surgical procedure, where a quadripolar tined lead is implanted for a testing phase to determine if patients show a sufficient reduction in symptom frequency, and if appropriate, proceeding to the permanent surgical implantation of a neuromodulation device. For testing phases and permanent implantation, determining the location of lead placement can be dependent on subjective qualitative analysis by either or both of a patient or a physician.

In exemplary embodiments, determination of whether or not an implantable lead and neurostimulation electrode is located in a desired or correct location can be accomplished through use of electromyography ("EMG"), also known as surface electromyography. EMG, is a technique that uses an EMG system or module to evaluate and record electrical activity produced by muscles, producing a record called an electromyogram. EMG detects the electrical potential generated by muscle cells when those cells are electrically or neurologically activated. The signals can be analyzed to detect activation level or recruitment order. EMG can be performed through the skin surface of a patient, intramuscularly or through electrodes disposed within a patient near target muscles, or using a combination of external and internal structures. When a muscle or nerve is stimulated by an electrode, EMG can be used to determine if the related muscle is activated, (i.e. whether the muscle fully contracts, partially contracts, or does not contract) in response to the stimulus. Accordingly, the degree of activation of a muscle can indicate whether an implantable lead or neurostimulation electrode is located in the desired or correct location on a patient. Further, the degree of activation of a muscle can indicate whether a neurostimulation electrode is providing a stimulus of sufficient strength, amplitude, frequency, or duration to affect a treatment regimen on a patient. Thus, use of EMG provides an objective and quantitative means by which to standardize placement of implantable leads and neurostimulation electrodes, reducing the subjective assessment of patient sensory responses.

In some approaches, positional titration procedures may optionally be based in part on a paresthesia or pain-based subjective response from a patient. In contrast, EMG triggers a measureable and discrete muscular reaction. As the efficacy of treatment often relies on precise placement of the neurostimulation electrodes at target tissue locations and the consistent, repeatable delivery of neurostimulation therapy, using an objective EMG measurement can substantially improve the utility and success of SNM treatment. The measureable muscular reaction can be a partial or a complete muscular contraction, including a response below the triggering of an observable motor response, such as those shown in Table 1, depending on the stimulation of the target muscle. In addition, by utilizing a trial system that allows the neurostimulation lead to remain implanted for use in the permanently implanted system, the efficacy and outcome of the permanently implanted system is more consistent with the results of the trial period, which moreover leads to improved patient outcomes.

C. Example Embodiments

FIG. 1 schematically illustrates an exemplary nerve stimulation system, which includes both a trial neurostimulation system 200 and a permanently implanted neurostimulation system 100, in accordance with aspects of the invention. The EPG 80 and IPG 10 are each compatible with and wirelessly communicate with a clinician programmer 60 and a patient remote 70, which are used in positioning and/or programming the trial neurostimulation system 200 and/or permanently implanted system 100 after a successful trial. As discussed above, the clinician programmer can include specialized software, specialized hardware, and/or both, to aid in lead placement, programming, re-programming, stimulation control, and/or parameter setting. In addition, each of the IPG and the EPG allows the patient at least some control over stimulation (e.g., initiating a pre-set program, increasing or decreasing stimulation), and/or to monitor battery status with the patient remote. This approach also allows for an almost seamless transition between the trial system and the permanent system.

In one aspect, the clinician programmer 60 is used by a physician to adjust the settings of the EPG and/or IPG while the lead is implanted within the patient. The clinician programmer can be a tablet computer used by the clinician to program the IPG, or to control the EPG during the trial period. The clinician programmer can also include capability to record stimulation-induced electromyograms to facilitate lead placement and programming. The patient remote 70 can allow the patient to turn the stimulation on or off, or to vary stimulation from the IPG while implanted, or from the EPG during the trial phase.

In another aspect, the clinician programmer 60 has a control unit which can include a microprocessor and specialized computer-code instructions for implementing methods and systems for use by a physician in deploying the treatment system and setting up treatment parameters. The clinician programmer generally includes a user interface which can be a graphical user interface, an EMG module, electrical contacts such as an EMG input that can couple to an EMG output stimulation cable, an EMG stimulation signal generator, and a stimulation power source. The stimulation cable can further be configured to couple to any or all of an access device (e.g., a foramen needle), a treatment lead of the system, or the like. The EMG input may be configured to be coupled with one or more sensory patch electrode(s) for attachment to the skin of the patient adjacent a muscle (e.g., a muscle enervated by a target nerve). Other connectors of the clinician programmer may be configured for coupling with an electrical ground or ground patch, an electrical pulse generator (e.g., an EPG or an IPG), or the like. As noted above, the clinician programmer can include a module with hardware and computer-code to execute EMG analysis, where the module can be a component of the control unit microprocessor, a pre-processing unit coupled to or in-line with the stimulation and/or sensory cables, or the like.

In some aspects, the clinician programmer is configured to operate in combination with an EPG when placing leads in a patient body. The clinician programmer can be electronically coupled to the EPG during test simulation through a specialized cable set. The test simulation cable set can connect the clinician programmer device to the EPG and allow the clinician programmer to configure, modify, or otherwise program the electrodes on the leads connected to the EPG.

The electrical pulses generated by the EPG and IPG are delivered to one or more targeted nerves via one or more neurostimulation electrodes at or near a distal end of each of one or more leads. The leads can have a variety of shapes, can be a variety of sizes, and can be made from a variety of materials, which size, shape, and materials can be tailored to the specific treatment application. While in this embodiment, the lead is of a suitable size and length to extend from the IPG and through one of the foramen of the sacrum to a targeted sacral nerve, in various other applications, the leads may be, for example, implanted in a peripheral portion of the patient's body, such as in the arms or legs, and can be configured to deliver electrical pulses to the peripheral nerve such as may be used to relieve chronic pain. It is appreciated that the leads and/or the stimulation programs may vary according to the nerves being targeted.

Figure 2A:
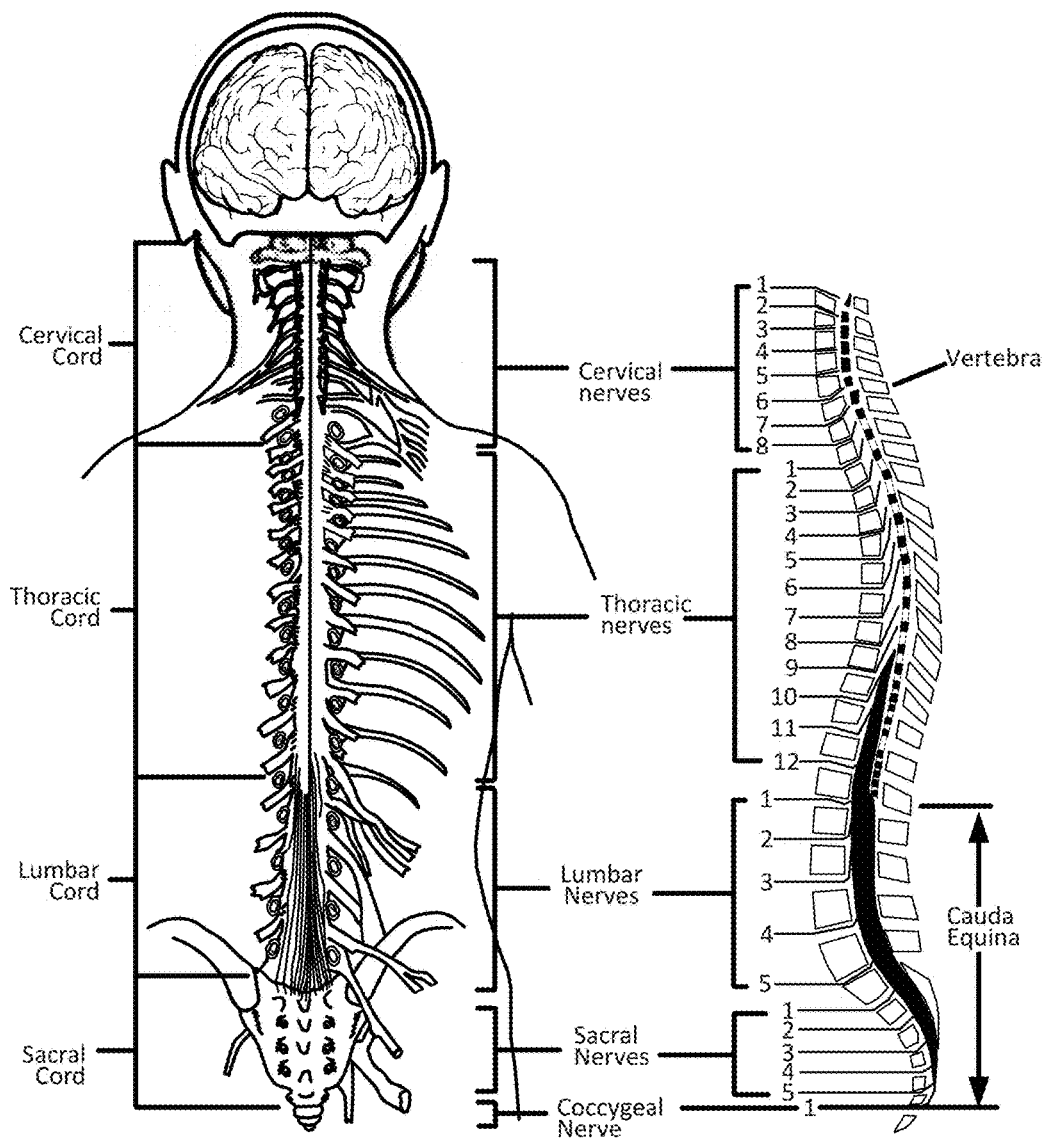
FIGS. 2A-2C show diagrams of the nerve structures along the spine, the lower back and sacrum region, which may be stimulated in accordance with aspects of the invention.
Figure 2B:
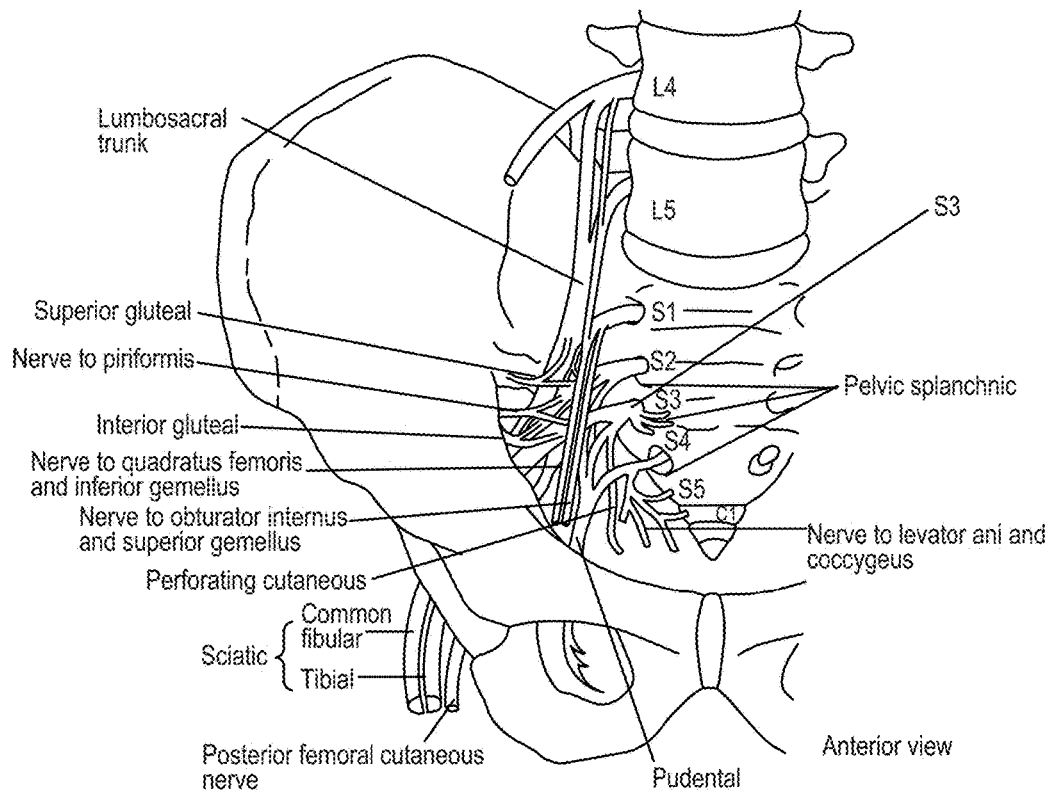
Figure 2C:
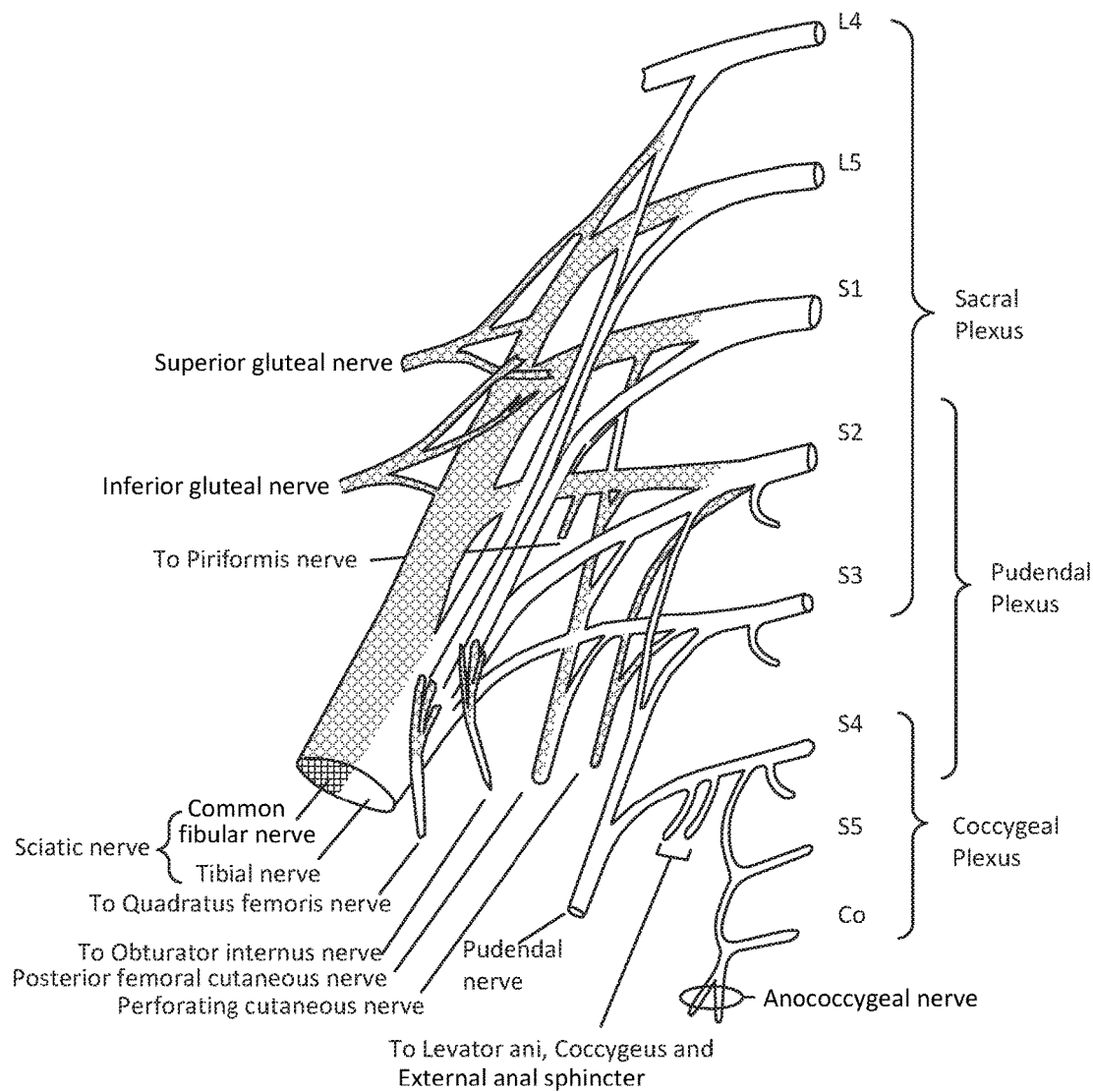

FIGS. 2A-2C show diagrams of various nerve structures of a patient, which may be used in neurostimulation treatments, in accordance with aspects of the invention. FIG. 2A shows the different sections of the spinal cord and the corresponding nerves within each section. The spinal cord is a long, thin bundle of nerves and support cells that extend from the brainstem along the cervical cord, through the thoracic cord and to the space between the first and second lumbar vertebra in the lumbar cord. Upon exiting the spinal cord, the nerve fibers split into multiple branches that innervate various muscles and organs transmitting impulses of sensation and control between the brain and the organs and muscles. Since certain nerves may include branches that innervate certain organs, such as the bladder, and branches that innervate certain muscles of the leg and foot, stimulation of the nerve at or near the nerve root near the spinal cord can stimulate the nerve branch that innervate the targeted organ, which may also result in muscle responses associated with the stimulation of the other nerve branch. Thus, by monitoring for certain muscle responses, such as those in Table 1, either visually, through the use of EMG as described herein or both, the physician can determine whether the targeted nerve is being stimulated. While stimulation at a certain threshold may trigger the noted muscle responses, stimulation at a sub-threshold level may still provide stimulation to the nerve associated with the targeted organ without causing the corresponding muscle response, and in some embodiments, without causing any paresthesia. This is advantageous as it allows for treatment of the condition by neurostimulation without otherwise causing patient discomfort, pain or undesired muscle responses.

FIG. 2B shows the nerves associated with the lower back section, in the lower lumbar cord region where the nerve bundles exit the spinal cord and travel through the sacral foramens of the sacrum. In some embodiments, the neurostimulation lead is advanced through the foramen until the neurostimulation electrodes are positioned at the anterior sacral nerve root, while the anchoring portion of the lead proximal of the stimulation electrodes are generally disposed dorsal of the sacral foramen through which the lead passes, so as to anchor the lead in position. FIG. 2C shows detail views of the nerves of the lumbosacral trunk and the sacral plexus, in particular, the S1-S5 nerves of the lower sacrum. The S3 sacral nerve is of particular interest for treatment of bladder related dysfunction, and in particular OAB.

FIG. 3A schematically illustrates an example of a fully implanted neurostimulation system 100 adapted for sacral nerve stimulation. Neurostimulation system 100 includes an IPG implanted in a lower back region and connected to a neurostimulation lead extending through the S3 foramen for stimulation of the S3 sacral nerve. The lead is anchored by a tined anchor portion 30 that maintains a position of a set of neurostimulation electrodes 40 along the targeted nerve, which in this example, is the anterior sacral nerve root S3 which enervates the bladder so as to provide therapy for various bladder related dysfunctions. While this embodiment is adapted for sacral nerve stimulation, it is appreciated that similar systems can be used in treating patients with, for example, chronic, severe, refractory neuropathic pain originating from peripheral nerves or various urinary dysfunctions or still further other indications. Implantable neurostimulation systems can be used to either stimulate a target peripheral nerve or the posterior epidural space of the spine.

Properties of the electrical pulses can be controlled via a controller of the implanted pulse generator. In some embodiments, these properties can include, for example, the frequency, strength, pattern, duration, or other aspects of the electrical pulses. These properties can include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In the embodiment depicted in FIG. 3A, the implantable neurostimulation system 100 includes a controller in the IPG having one or more pulse programs, plans, or patterns that may be pre-programmed or created as discussed above. In some embodiments, these same properties associated with the IPG may be used in an EPG of a partly implanted trial system used before implantation of the permanent neurostimulation system 100.

Figure 3B:
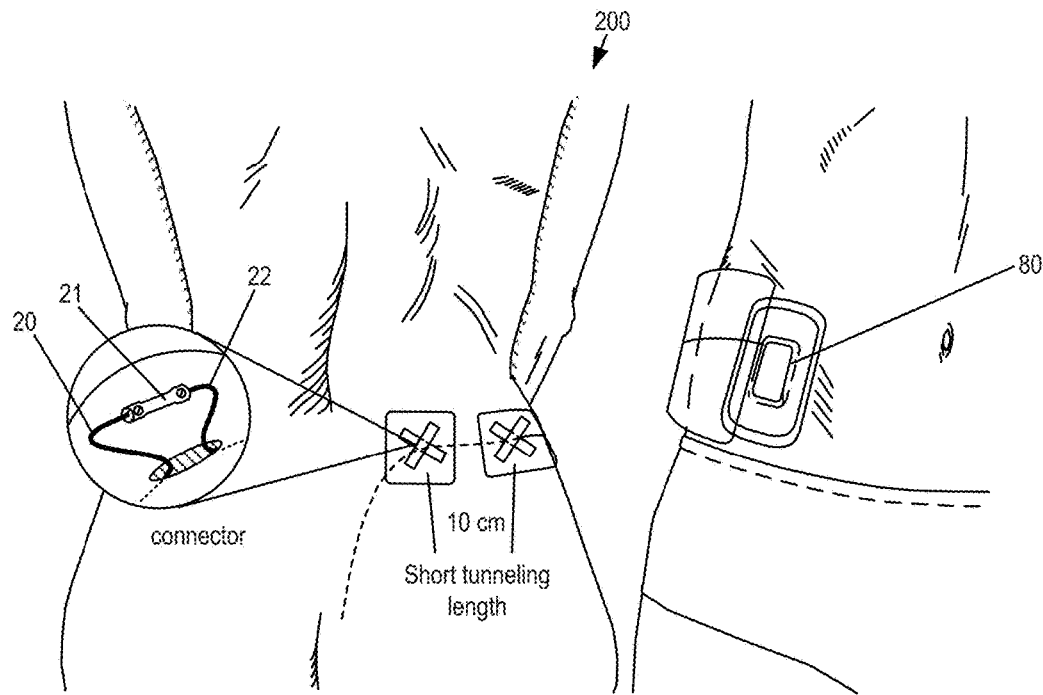
FIG. 3B shows an example of a neurostimulation system having a partly implanted stimulation lead and an external pulse generator adhered to the skin of the patient for use in a trial stimulation, in accordance with aspects of the invention.
Figure 3B:
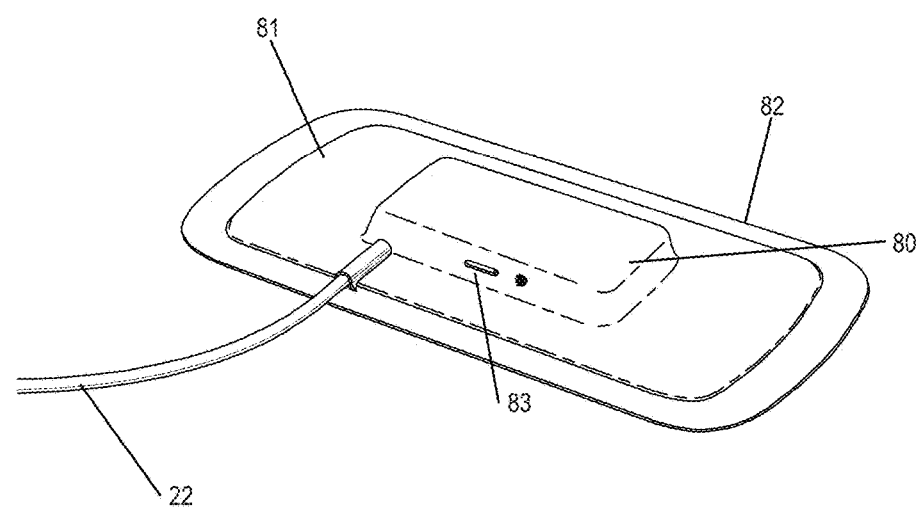

FIG. 3B shows a schematic illustration of a trial neurostimulation system 200 utilizing an EPG patch 81 adhered to the skin of a patient, particularly to the abdomen of a patient, the EPG 80 being encased within the patch. In one aspect, the lead is hardwired to the EPG, while in another the lead is removably coupled to the EPG through a port or aperture in the top surface of the flexible patch 81. Excess lead can be secured by an additional adherent patch. In one aspect, the EPG patch is disposable such that the lead can be disconnected and used in a permanently implanted system without removing the distal end of the lead from the target location. Alternatively, the entire system can be disposable and replaced with a permanent lead and IPG. When the lead of the trial system is implanted, an EMG obtained via the clinician programmer using one or more sensor patches can be used to ensure that the leads are placed at a location proximate to the target nerve or muscle, as discussed previously.

In some embodiments, the trial neurostimulation system utilizes an EPG 80 within an EPG patch 81 that is adhered to the skin of a patient and is coupled to the implanted neurostimulation lead 20 through a lead extension 22, which is coupled with the lead 20 through a connector 21. This extension and connector structure allows the lead to be extended so that the EPG patch can be placed on the abdomen and allows use of a lead having a length suitable for permanent implantation should the trial prove successful. This approach may utilize two percutaneous incisions, the connector provided in the first incision and the lead extensions extending through the second percutaneous incision, there being a short tunneling distance (e.g., about 10 cm) there between. This technique may also minimize movement of an implanted lead during conversion of the trial system to a permanently implanted system.

In one aspect, the EPG unit is wirelessly controlled by a patient remote and/or the clinician programmer in a similar or identical manner as the IPG of a permanently implanted system. The physician or patient may alter treatment provided by the EPG through use of such portable remotes or programmers and the treatments delivered are recorded on a memory of the programmer for use in determining a treatment suitable for use in a permanently implanted system. The clinician programmer can be used in lead placement, programming and/or stimulation control in each of the trial and permanent nerve stimulation systems. In addition, each nerve stimulation system allows the patient to control stimulation or monitor battery status with the patient remote. This configuration is advantageous as it allows for an almost seamless transition between the trial system and the permanent system. From the patient's viewpoint, the systems will operate in the same manner and be controlled in the same manner, such that the patient's subjective experience in using the trial system more closely matches what would be experienced in using the permanently implanted system. Thus, this configuration reduces any uncertainties the patient may have as to how the system will operate and be controlled such that the patient will be more likely to convert a trial system to a permanent system.

As shown in the detailed view of FIG. 3B, the EPG 80 is encased within a flexible laminated patch 81, which include an aperture or port through which the EPG 80 is connected to the lead extension 22. The patch may further an "on/off" button 83 with a molded tactile detail to allow the patient to turn the EPG on and/or off through the outside surface of the adherent patch 81. The underside of the patch 81 is covered with a skin-compatible adhesive 82 for continuous adhesion to a patient for the duration of the trial period. For example, a breathable strip having skin-compatible adhesive 82 would allow the EPG 80 to remain attached to the patient continuously during the trial, which may last over a week, typically two weeks to four weeks, or even longer.

Figure 4:
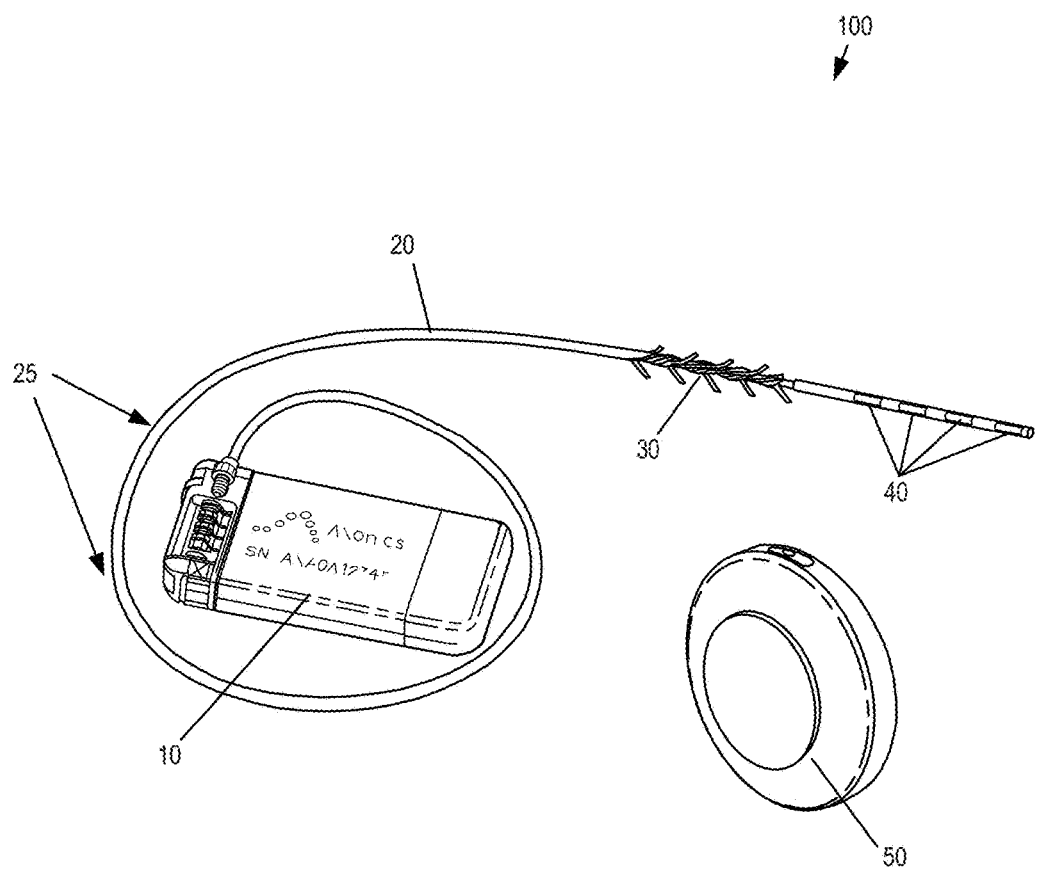
FIG. 4 shows an example of a neurostimulation system having an implantable stimulation lead, an implantable pulse generator, and an external charging device, in accordance with aspects of the invention.

FIG. 4 illustrates an example neurostimulation system 100 that is fully implantable and adapted for sacral nerve stimulation treatment. The implantable system 100 includes an IPG 10 that is coupled to a neurostimulation lead 20 that includes a group of neurostimulation electrodes 40 at a distal end of the lead. The lead includes a lead anchor portion 30 with a series of tines extending radially outward so as to anchor the lead and maintain a position of the neurostimulation lead 20 after implantation. The lead 20 may further include one or more radiopaque markers 25 to assist in locating and positioning the lead using visualization techniques such as fluoroscopy. In some embodiments, the IPG provides monopolar or bipolar electrical pulses that are delivered to the targeted nerves through one or more neurostimulation electrodes, typically four electrodes. In sacral nerve stimulation, the lead is typically implanted through the S3 foramen as described herein.

Figure 6:
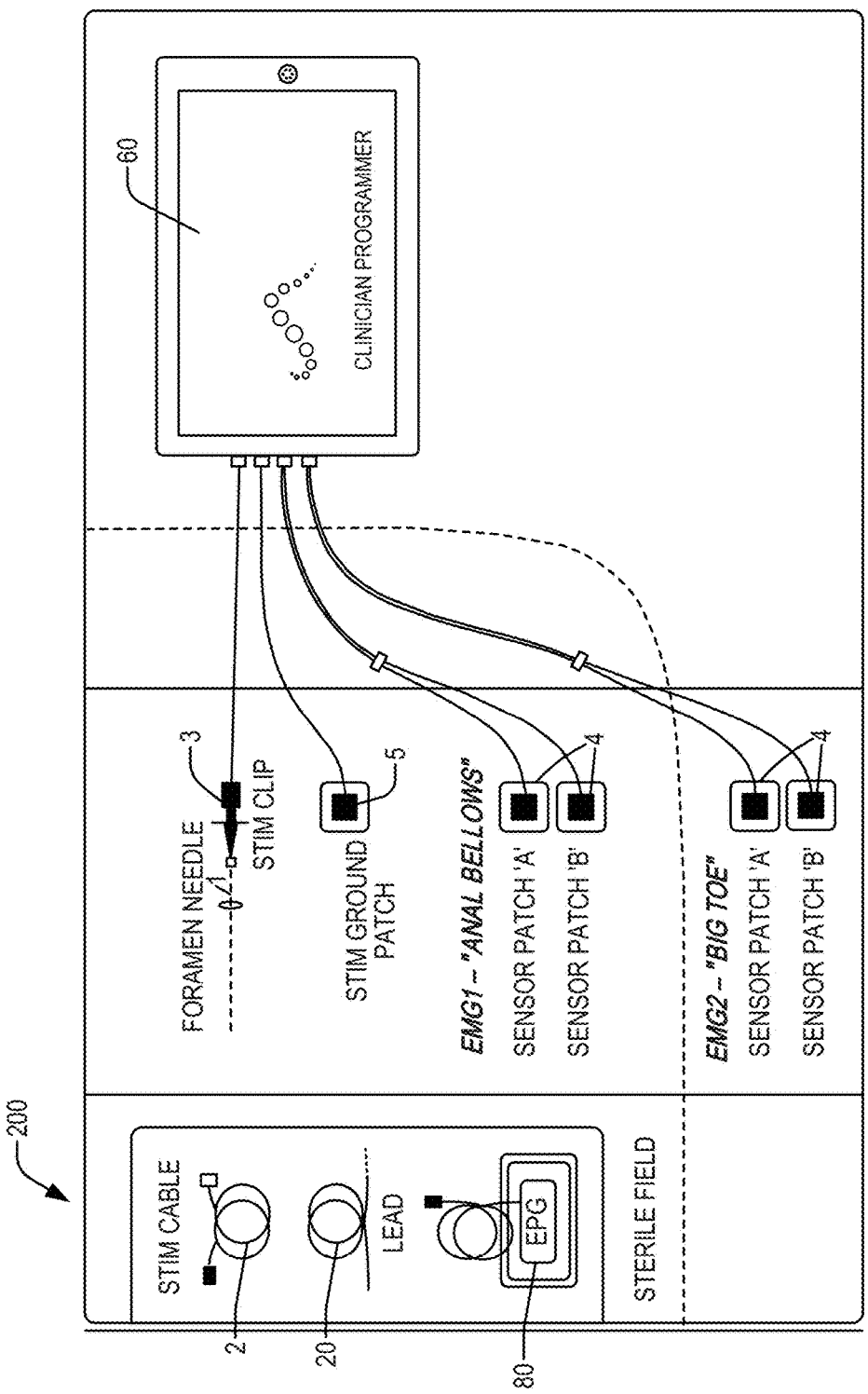
FIG. 6 schematically illustrates a nerve stimulation system utilizing a control unit with a stimulation clip, a ground patch, two electromyography sensors, and ground patch sets connected during the operation of placing a trial or permanent neurostimulation system, in accordance with aspects of the invention.

In one aspect, the IPG is rechargeable wirelessly through conductive coupling by use of a charging device 50 (CD), which is a portable device powered by a rechargeable battery to allow patient mobility while charging. The CD is used for transcutaneous charging of the IPG through RF induction. The CD can be either patched to the patient's skin using an adhesive or can be held in place using a belt 53 or by an adhesive patch 52, such as shown in the schematic of FIG. 6. The CD may be charged by plugging the CD directly into an outlet or by placing the CD in a charging dock or station 51 that connects to an AC wall outlet or other power source.

Figure 5A:
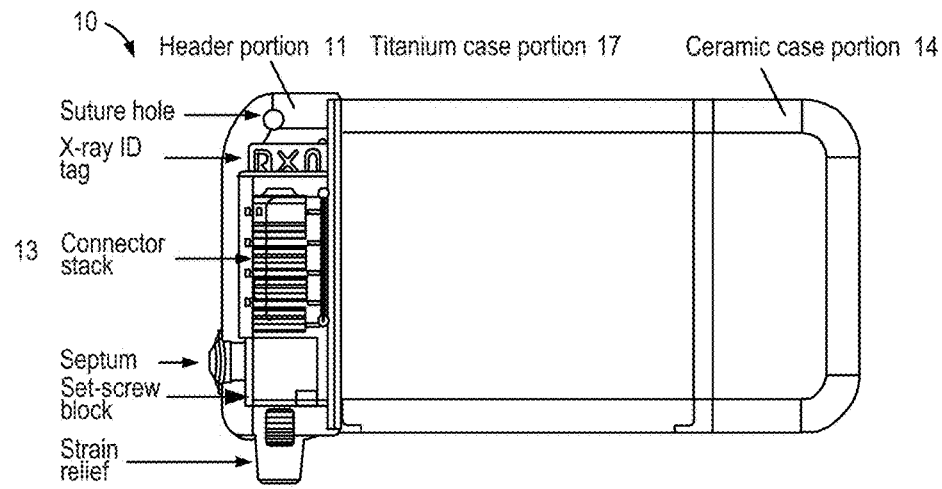
FIG. 5A-5C show detail views of an implantable pulse generator and associated components for use in a neurostimulation system, in accordance with aspects of the invention.
Figure 5B:
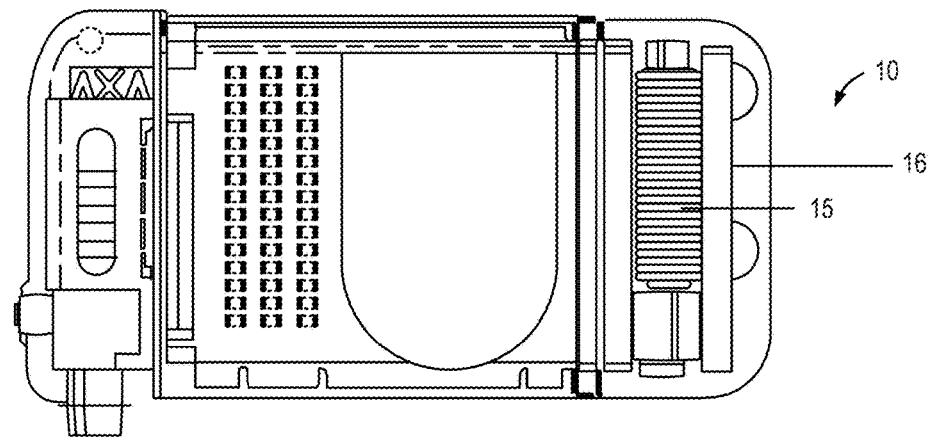
Figure 5C:
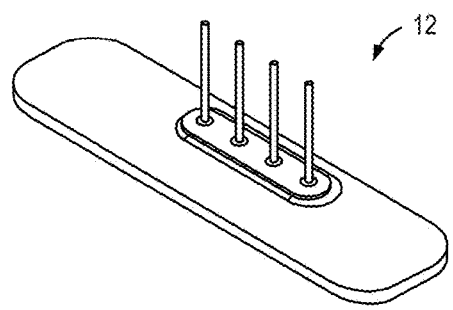

The system may further include a patient remote 70 and clinician programmer 60, each configured to wirelessly communicate with the implanted IPG, or with the EPG during a trial, as shown in the schematic of the nerve stimulation system in FIG. 6. The clinician programmer 60 may be a tablet computer used by the clinician to program the IPG and the EPG. The device also has the capability to record stimulation-induced electromyograms (EMGs) to facilitate lead placement, programming, and/or re-programming. The patient remote may be a battery-operated, portable device that utilizes radio-frequency (RF) signals to communicate with the EPG and IPG and allows the patient to adjust the stimulation levels, check the status of the IPG battery level, and/or to turn the stimulation on or off FIG. 5A-5C show detail views of the IPG and its internal components. In some embodiments, the pulse generator can generate one or more non-ablative electrical pulses that are delivered to a nerve to control pain or cause some other desired effect, for example to inhibit, prevent, or disrupt neural activity for the treatment of OAB or bladder related dysfunction. In some applications, the pulses having a pulse amplitude in a range between 0 mA to 1,000 mA, 0 mA to 100 mA, 0 mA to 50 mA, 0 mA to 25 mA, and/or any other or intermediate range of amplitudes may be used. One or more of the pulse generators can include a processor and/or memory adapted to provide instructions to and receive information from the other components of the implantable neurostimulation system. The processor can include a microprocessor, such as a commercially available microprocessor from Intel® or Advanced Micro Devices, Inc.®, or the like. An IPG may include an energy storage feature, such as one or more capacitors, and typically includes a wireless charging unit.

One or more properties of the electrical pulses can be controlled via a controller of the IPG or EPG. In some embodiments, these properties can include, for example, the frequency, strength, pattern, duration, or other aspects of the timing and magnitude of the electrical pulses. These properties can further include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In one aspect, the IPG 10 includes a controller having one or more pulse programs, plans, or patterns that may be created and/or pre-programmed. In some embodiments, the IPG can be programmed to vary stimulation parameters including pulse amplitude in a range from 0 mA to 10 mA, pulse width in a range from 50 µs to 500 µs, pulse frequency in a range from 5 Hz to 250 Hz, stimulation modes (e.g., continuous or cycling), and electrode configuration (e.g., anode, cathode, or off), to achieve the optimal therapeutic outcome specific to the patient. In particular, this allows for an optimal setting to be determined for each patient even though each parameter may vary from person to person.

As shown in FIGS. 5A-5B, the IPG may include a header portion 11 at one end and a ceramic portion 14 at the opposite end. The header portion 11 houses a feed through assembly 12 and connector stack 13, while the ceramic case portion 14 houses an antenna assembly 16 to facilitate wireless communication with the clinician program, the patient remote, and/or a charging coil to facilitate wireless charging with the CD. The remainder of the IPG is covered with a titanium case portion 17, which encases the printed circuit board, memory and controller components that facilitate the electrical pulse programs described above. In the example shown in FIG. 5C, the header portion of the IPG includes a four-pin feed-through assembly 12 that couples with the connector stack 13 in which the proximal end of the lead is coupled. The four pins correspond to the four electrodes of the neurostimulation lead. In some embodiments, a Balseal® connector block is electrically connected to four platinum/iridium alloy feed-through pins which are brazed to an alumina ceramic insulator plate along with a titanium alloy flange. This feed-through assembly is laser seam welded to a titanium-ceramic brazed case to form a complete hermetic housing for the electronics. The number of header electrical contacts is a function of the number of electrodes and leads used for any particular system configuration.

In some embodiment, such as that shown in FIG. 5A, the ceramic and titanium brazed case is utilized on one end of the IPG where the ferrite coil and PCB antenna assemblies are positioned. A reliable hermetic seal is provided via a ceramic-to-metal brazing technique. The zirconia ceramic may comprise a 3Y-TZP (3 mol percent Yttria-stabilized tetragonal Zirconia Polycrystals) ceramic, which has a high flexural strength and impact resistance and has been commercially utilized in a number of implantable medical technologies. It will be appreciated, however, that other ceramics or other suitable materials may be used for construction of the IPG.

In one aspect, utilization of ceramic material provides an efficient, radio-frequency-transparent window for wireless communication with the external patient remote and clinician's programmer as the communication antenna is housed inside the hermetic ceramic case. This ceramic window has further facilitated miniaturization of the implant while maintaining an efficient, radio-frequency-transparent window for long term and reliable wireless communication between the IPG and external controllers, such as the patient remote and clinician programmer. The IPG's wireless communication is generally stable over the lifetime of the device, unlike prior art products where the communication antenna is placed in the header outside the hermetic case. The communication reliability of such prior art devices tends to degrade due to the change in dielectric constant of the header material in the human body over time.

In another aspect, the ferrite core is part of the charging coil assembly 15, shown in FIG. 5B, which is positioned inside the ceramic case 14. The ferrite core concentrates the magnetic field flux through the ceramic case as opposed to the metallic case portion 17. This configuration maximizes coupling efficiency, which reduces the required magnetic field and in turn reduces device heating during charging. In particular, because the magnetic field flux is oriented in a direction perpendicular to the smallest metallic cross section area, heating during charging is minimized. This configuration also allows the IPG to be effectively charged at depth of 3 cm with the CD, when positioned on a skin surface of the patient near the IPG and reduces re-charging time.

FIG. 6 shows a setup for a test stimulation and EMG sensing using a clinician programmer 60. As discussed above, the clinician programmer 60 is a tablet computer with software that runs on a standard operating system. The clinician programmer 60 includes a communication module, a stimulation module and an EMG sensing module. The communication module communicates with the IPG and/or EPG in the medical implant communication service frequency band for programming the IPG and/or EPG.

In order to confirm correct lead placement, it is desirable for the physician to confirm that the patient has both adequate motor and sensory responses before transitioning the patient into the staged trial phase or implanting the permanent IPG. However, sensory response is a subjective evaluation and may not always be available, such as when the patient is under general anesthesia. Experiments have shown that demonstrating appropriate motor responses is advantageous for accurate placement, even if sensory responses are available. As discussed above, EMG is a tool which records electrical activity of skeletal muscles. This sensing feature provides an objective criterion for the clinician to determine if the sacral nerve stimulation results in adequate motor response rather than relying solely on subjective sensory criteria. EMG can be used not only to verify optimal lead position during lead placement, but also to provide a standardized and more accurate approach to determine electrode thresholds, which in turn provides quantitative information supporting electrode selection for programming. Using EMG to verify activation of motor responses can further improve the lead placement performance of less experienced operators and allow such physicians to perform lead placement with confidence and greater accuracy.

In one aspect, the system is configured to have EMG sensing capability during re-programming, which can be particularly valuable. Stimulation levels during re-programming are typically low to avoid patient discomfort which often results in difficult generation of motor responses. Involuntary muscle movement while the patient is awake may also cause noise that is difficult for the physician to differentiate. In contrast to conventional approaches, EMG allows the clinician to detect motor responses at very low stimulation levels (e.g., sub-threshold), and help them distinguish a motor response originated by sacral nerve stimulation from involuntary muscle movement.

Referring to FIG. 6, several cable sets are connected to the CP. The stimulation cable set consists of one stimulation mini-clip 3 and one ground patch 5. It is used with a foramen needle 1 to locate the sacral nerve and verify the integrity of the nerve via test stimulation. Another stimulation cable set with four stimulation channels 2 is used to verify the lead position with a tined stimulation lead 20 during the staged trial. Both cable sets are sterilizable as they will be in the sterile field. A total of five over-the-shelf sensing electrode patches 4 (e.g., two sensing electrode pairs for each sensing spot and one common ground patch) are provided for EMG sensing at two different muscle groups (e.g., perineal musculature and big toe) simultaneously during the lead placement procedure. This provides the clinician with a convenient all-in-one setup via the EMG integrated clinician programmer. Typically, only one electrode set (e.g., two sensing electrodes and one ground patch) is needed for detecting an EMG signal on the big toe during an initial electrode configuration and/or re-programming session. Typically, these over-the-shelf EMG electrodes are also provided sterile though not all cables are required to be connected to the sterile field. The clinician programmer 60 allows the clinician to read the impedance of each electrode contact whenever the lead is connected to an EPG, an IPG or a clinician programmer to ensure reliable connection is made and the lead is intact. In some embodiments, any electrode with unacceptable impedance can be locked out from being assigned as an anode or cathode. Unacceptable impedance can be impedance less than 50 or greater than 3,000 Ohms, or alternatively less than 500 or greater than 5,000 Ohms. The clinician programmer 60 is also able to save and display previous (e.g., up to the last four) programs that were used by a patient to help facilitate re-programming. In some embodiments, the clinician programmer 60 further includes a USB port for saving reports to a USB drive and a charging port. The clinician programmer may also include physical on/off buttons to turn the clinician programmer on and off and/or to turn stimulation on and off.

Figure 7:
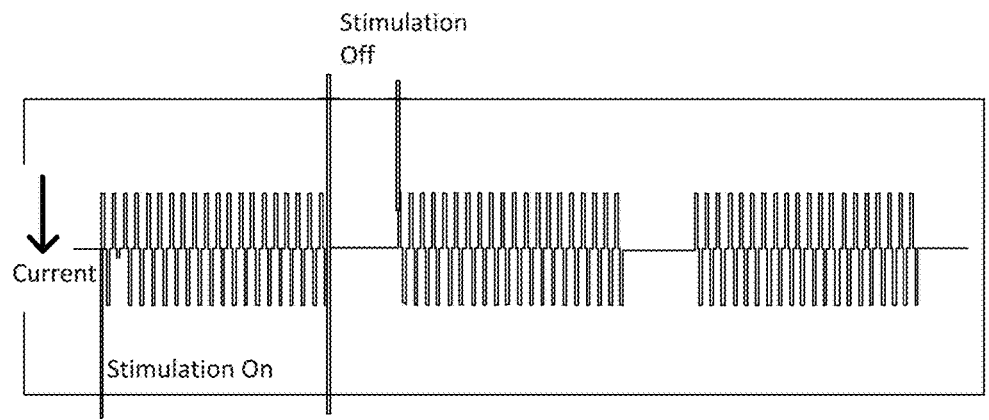
FIGS. 7-8 show signal characteristics of a neurostimulation program, in accordance with aspects of the invention.

In some embodiments, the IPG, as well as the EPG, may be configured with two stimulation modes: continuous mode and cycling mode, such as shown in FIG. 7. The cycling mode saves energy in comparison to the continuous mode, thereby extending the recharge interval of the battery and lifetime of the device. The cycling mode may also help reduce the risk of neural adaptation for some patients. Neural adaptation is a change over time in the responsiveness of the neural system to a constant stimulus. Thus, cycling mode may also mitigate neural adaptation so to provide longer-term therapeutic benefit. FIG. 7 shows an example of stimulation in a cycling mode, in which the duty cycle is the stimulation on time over the stimulation-on time plus the stimulation-off time.

Figure 8:
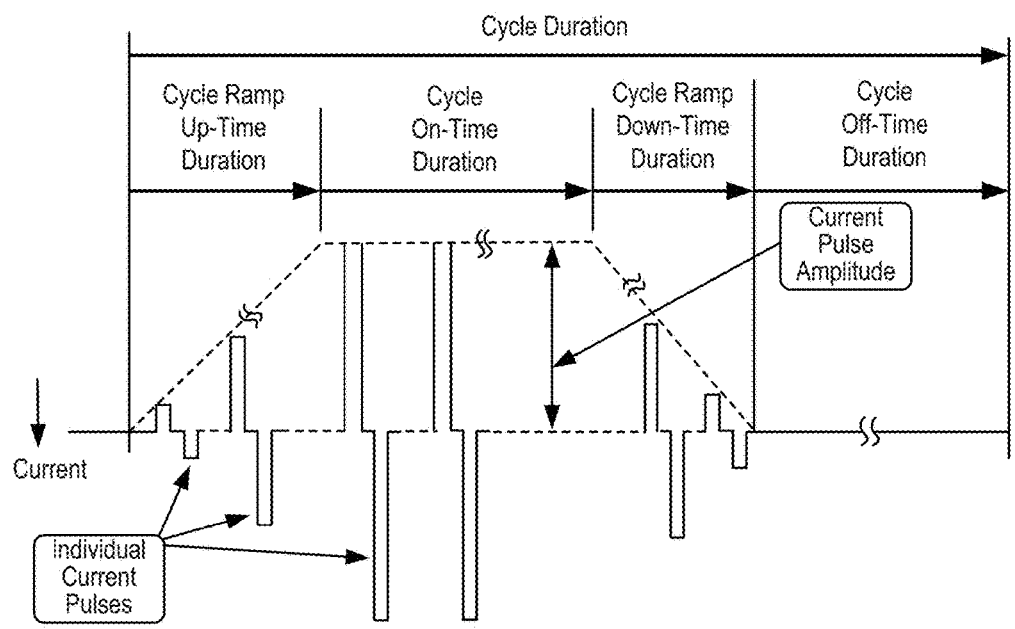

In some embodiments, the IPG/EPG is configured with a ramping feature, such as shown in the example of FIG. 8. In these embodiments, the stimulation signal is ramped up and/or down between the stimulation-on and stimulation-off levels. This feature helps reduce the sudden "jolting" or "shocking" sensation that some patients might experience when the stimulation is initially turned on or at the cycle-on phase during the cycling mode. This feature is particularly of benefit for patients who need relative high stimulation settings and/or for patients who are sensitive to electrical stimulation.

D. Patient Remote Control

The patient remote (e.g. FIG. 1, element 70) is provided to allow a patient to adjust the stimulation level of the electrical pulse generator. The patient remote can be used to wirelessly communicate with and control either an EPG (e.g., during a trial phase) or an IPG (e.g., for a permanent neurostimulation system). In some implementations, different patient remotes can be provided to control the EPG and the IPG, whereas in other implementations, a single patient remote can be programmed or reprogrammed to control either an EPG or an IPG. A particular patient remote can be configured to link with and wirelessly communicate with only a single EPG or IPG so as to avoid patients altering the stimulation of others.

The degree of adjustment permitted to the patient through the patient remote can be limited, such that while the patient can incrementally increase or decrease the therapy delivered by the pulse generator, and can turn stimulation on or off, the level of stimulation therapy by the pulse generator whenever the pulse generator is applying stimulation is maintained within a clinically effective combination of settings. By providing a limited range of adjustment to a patient through the patient remote, the patient is given a straightforward and simple tool for situational control of the pulse generator and overall neurostimulation system, allowing for the use of different stimulation levels (including no stimulation when appropriate) while the patient is awake, while the patient is asleep, while the patient is engaged in specific activities, or in other situations. However, the patient may not be presented with a selection of alternative therapies or multivariate operational programs via the patient remote that may confuse the patient or take the pulse generator outside of a clinically effective range. In some aspects, the patient remote can be configured to provide monovariant control to the patient. For example, the patient remote can be limited to varying a stimulation level of the stimulation program, while the other attributes of the stimulation program (e.g. duration, electrode configuration, pulse width, etc.) are maintained. The clinically effective range of the pulse generator can be determined by a physician or the clinician programmer when setting the parameters of the pulse generator and neurostimulation system.

The patient remote can allow a patient to turn on and turn off the pulse generator, where turning off the pulse generator may be desirable for the patient when performing activities that may inadvertently interfere with, or be inadvertently interfered by, an active pulse generator and the nerves stimulated by the pulse generator. For example, as noted in Table 1 above, innervation of the S3 sacral nerve can cause a response in the plantar flexion of the great toe or other toes. Thus, it may be desirable to provide a patient the option to turn off the pulse generator while driving, carrying heavy objects, or performing other activities that can strain the foot or toes and may thereby inadvertently trigger a pulling sensation in the rectum. Moreover, it may be desirable to provide a patient the option to automatically restore the pulse generator to a previous level of stimulation when the pulse generator is turned on after a period of being turned off. In many cases, the previous level of stimulation can be the last stored stimulation level of the patient remote. In further implementations, the patient remote can provide the patient with an indication of battery status and/or therapy remaining for the neurostimulation system and pulse generator.

Structurally, the patient remote can include a portable housing, with one or more switches and one or more displays on or embedded within the exterior surface of the portable housing. The patient remote can have an activation switch and a stimulation-increase switch disposed on an exterior surface of the patient remote, allowing the patient (or other operator) to activate the patient remote and then to instruct the neurostimulation system to increase the stimulation level of the pulse generator. The patent remote can also include any combination of a stimulation-decrease switch (allowing the patient to decrease the stimulation level), a stimulation-level display, a therapy-remaining display, and/or a fault condition display disposed on the exterior surface of the patient remote.

In other words, the portable housing of the patient remote can be sized or dimensioned so as to fit within a single hand of a patient. The patient remote can accordingly be operable within a single hand of a patient, or another operator. Further, in the context of the present disclosure, the switches of the patient remote can instead be buttons, formed as part of the body of the patient remote, or formed to pass through shaped holes in the surface of the patient remote. In implementations of the patient remote having buttons, the buttons can be spring biased or otherwise supported so as to provide a degree of resistance to actuation and/or to restore a button to a default status after actuation is completed and the button is released. Any given switch or button on the patient remote can be located within a depression of the external surface of the patient remote, on a flat surface of the external surface of the patient remote, or on a convex surface of the external surface of the patient remote. Moreover, any given switch or button on the patient remote can have a profile that is flush with the external surface of the patient remote, elevated from the external surface of the patient remote, or inset/depressed within the external surface of the patient remote.

While the terms "switches" and "buttons" are used in the described embodiments to illustrate various concepts, it is appreciated that such terms can encompass any actuation feature that is operable by a user to effect a change in state associated with the patient remote. A change in state can include a change in an activation state of the patient remote, or a mode of the pulse generator and a stimulation level of the IPG or EPG that is controlled by the patient remote. For example, the actuation feature can be a button, lever, knob, or an optical or touch sensor or any suitable feature that allows a user to effect the change in state by interaction with the feature. In some embodiments, the actuation features can include portions of a touch screen displayed to a user.

Figure 9:
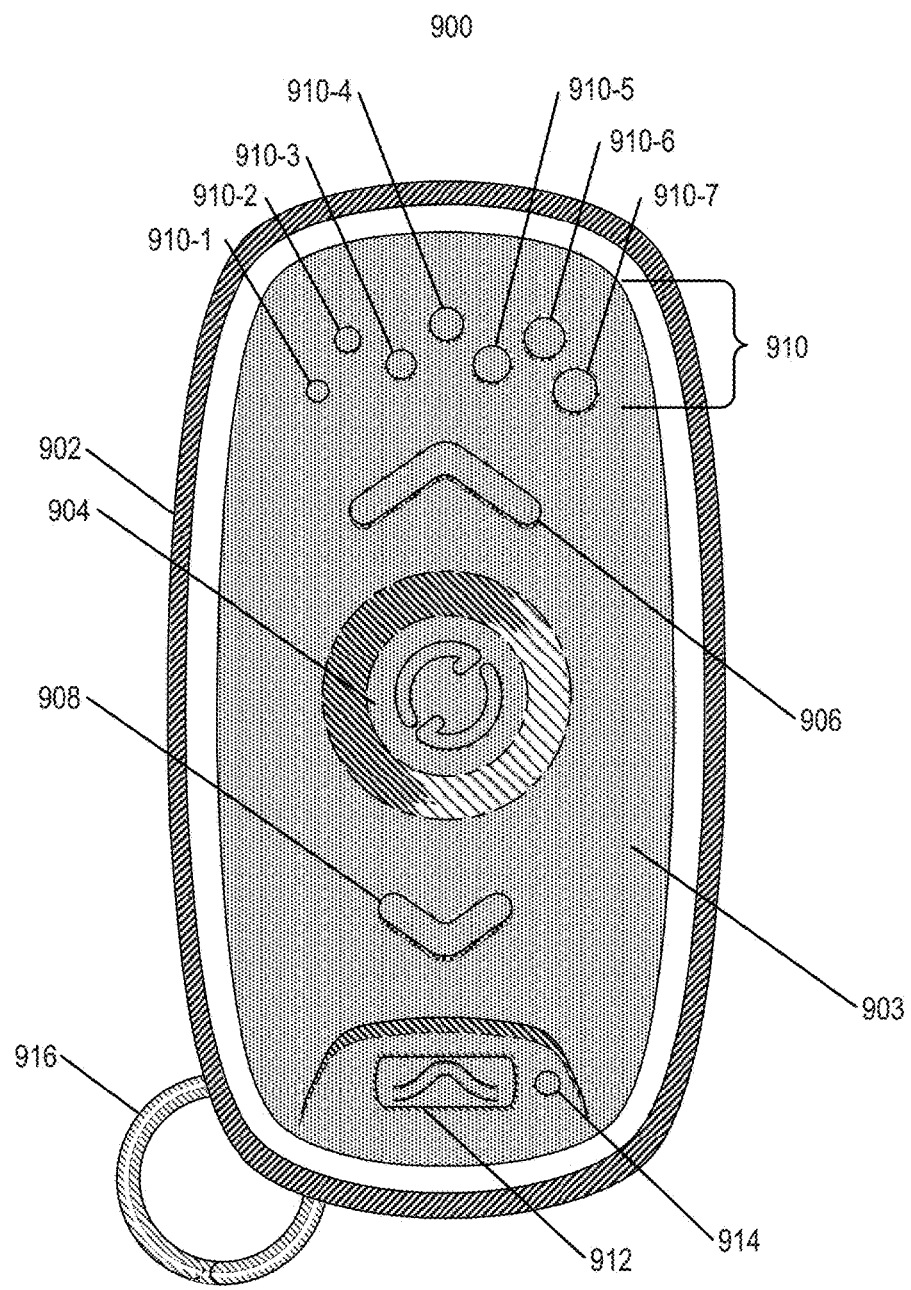
FIG. 9 is a schematic illustration of a patient remote, in accordance with aspects of the invention.

FIG. 9 is a schematic illustration of a patient remote 900 showing the structure of a portable housing 902. The portable housing 902 has an exterior surface, and in many embodiments the patient remote 900 can have a control surface 903 on a top side of the exterior surface where operational switches and display elements can be disposed. In various aspects, the control surface 903 can be constructed of a material that is the same or different as the rest of the portable housing 902. In other embodiments, the portable housing 902 can have operational switches or display elements on a bottom side or lateral sides of the portable housing 902. The portable housing 902 can be constructed from plastics, lightweight metals (e.g., aluminum), or a combination thereof, and can be designed and constructed to be of a size such that the patient remote 900 can be held and operated in a single hand of a patient. The patient remote 900 can have an oblong, elongated, rectangular, spherical, square, ellipsoid, or irregular shape, or a combination thereof. The patient remote 900 can be constructed to be waterproof, where any structural seams of the portable housing 902 can have an airtight interface or sealed with an additional polymer or chemical compound. The portable housing 902 can further be designed to attach as a fob device, configured to be carried daily, having a mechanical coupling structure 916 to attach the patient remote 900 with a key ring, karabiner, or other such mounting element.

The patient remote 900 can include within the interior of the portable housing 902 transmission circuitry configured to interface with the pulse generator, a battery that functions as a power source for the patient remote, and control electronics. Control electronics in the interior of the portable housing 902 can be operatively coupled to relay signals to the transmission circuitry for controlling control the pulse generator corresponding to actuation of the one or more switches disposed on the exterior surface of the portable housing 902. In alternative aspects, the patient remote 900 can include circuitry to communicate with the clinician programmer (CP).

The transmission circuitry can include a radio frequency (RF) transmitter that communicates with other system elements on the Medical Implant Communication Service (MICS) frequency band (MedRadio 402-405 MHz). The wireless communication between the patient remote 900 and the pulse generator to which the patient remote 900 sends instructions can have an operational range of up to three feet, in addition to transmission through the tissue of a patient, in embodiments where the pulse generator is an IPG implanted in the patient. A patient remote 900 having any or all of an activation switch 904, stimulation-increase switch 906, or stimulation-decrease switch 908 (where any or all of activation switch 904, stimulation-increase switch 906, or stimulation-decrease switch 908 can be buttons) disposed on the exterior surface of the portable housing 902 can be configured such that actuation of such switches and/or buttons (where actuation can be depressing, triggering, toggling, or otherwise operating the switch or button) causes the control electronics and/or transmission circuitry of the patient remote 900 to relay a signal to a neurostimulation system and/or to execute a function of the patient remote 900 itself. In some aspects, the battery that powers the patient remote 900 can be a permanent battery having an operational life of three or more years. In alternative aspects, the battery that powers the patient remote 900 can be a replaceable or a rechargeable battery.

In some embodiments, the activation switch 904 (alternatively referred to as a "link switch") can be disposed on the control surface 903, and in particular embodiments the activation switch 904 can be disposed in a recessed region of the control surface 903. In embodiments where the activation switch 904 is disposed in a recess of the control surface 903, activation switch 904 is designed to be actuation due to deliberate effort. In other words, where the structure of the activation switch 904 is disposed within the recess, accidental or inadvertent actuation of the activation switch 904 due to incidental physical contact with the exterior surface of the portable housing 902 or contact with other sections of the control surface 903 can be avoided by providing sufficient physical resistance to a throw of the switch. More succinctly, in various embodiments, the activation switch 904 is recessed so as to avoid accidental depression by the user when the patient remote 900 is stored in a pocket or purse of the patient. In these embodiments, the recess can have a sufficient depth relative to the size of the activation switch 904 such that the height of the activation switch 904 is shorter than the depth of the recess, and thus the activation switch 904 does not extend out of the recess.

The activation switch 904 operates to switch the patient remote 900 between an asleep mode and an awake mode. When the patient remote 900 is in an asleep mode, actuation of the activation switch 904 causes the patient remote to switch to the awake mode and to interrogate the neurostimulator to wirelessly retrieve data regarding the status of the neurostimulation system and/or pulse generator. The data retrieved from the neurostimulation system can include the current stimulation level of the pulse generator, which can be stored in a processor and/or memory of the pulse generator. When the patient remote 900 is in the awake mode, actuation of the activation switch 904 causes the patient remote 900 to switch to the asleep mode. When the patient remote 900 is in the asleep mode, the stimulation-increase switch 906 and the stimulation-decrease switch 908 (both also disposed on the control surface 903) are inactivated, such that actuation of either the stimulation-increase switch 906 or the stimulation-decrease switch 908 does not cause the patient remote 900 to send any signal with transmission circuitry within the portable housing 902. When the patient remote 900 is in the awake mode, the stimulation-increase switch 906 and the stimulation-decrease switch 908 are active, such that actuation of either the stimulation-increase switch 906 or the stimulation-decrease switch 908 causes the patient remote 900 to send a corresponding instruction signal with transmission circuitry within the portable housing 902. When in the awake mode, if the patient remote 900 is inactive for a set period of time (e.g. none of the activation switch 904, stimulation-increase switch 906, or stimulation-decrease switch 908 are actuated for the set period of time), the patient remote can automatically switch to the asleep mode. In some aspects, the set period of time after which the patient remote 900 will automatically switch to the asleep mode can be five (5) to sixty (60) seconds, or any increment or gradient of time within that range. In specific aspects, the set period of time after which the patient remote 900 will automatically switch to the asleep mode can be ten (10) seconds.

The control surface 903 can include a stimulation-increase switch 906 coupled to control electronics and transmission circuitry disposed within the portable housing 902. Actuation of the stimulation-increase switch 906 can relay an instruction signal to the pulse generator (i.e., through the control electronics and transmission circuitry of the patient remote 900), where the instruction signal can be selected based on duration of time that the stimulation-increase switch 906 is actuated. When the stimulation-increase switch 906 is actuated for a first period of time, the patient remote 902 can send an instruction signal to the pulse generator to incrementally increase the stimulation level of the pulse generator. The first period of time will generally be a period of time that is shorter than a threshold. The threshold may generally be between 0.25 and 5 seconds, with the time period for a longer switch actuation threshold time being sufficient to assure that the longer duration switch actuation is clearly intentional, typically being three seconds or more. Increasing the stimulation level of the pulse generator can be limited to a maximum selectable level of therapy. When the stimulation-increase switch 906 is actuated for a second, longer period of time, the patient remote 902 can send an instruction signal to the pulse generator to restore the stimulation level of the pulse generator to a previously stored stimulation level. The second period of time can be three seconds or more. In some aspects, when the pulse generator is instructed to restore the previously stored stimulation level, the pulse generator can gradually ramp up (as shown in FIG. 8) to help reduce any sudden "jolting" or "shocking" sensation that some patients might experience when the stimulation is turned on.

In situations where a patient has turned off the pulse generator, providing a method to automatically return the stimulation of the pulse generator to a previously stored stimulation level allows a patient to efficiently and automatically restore the neurostimulation system to a desired function or status, avoiding the need for repetitive adjustment of the stimulation level. In many embodiments, the previously stored stimulation level can be the last stimulation level the pulse generator was set to before turning off the neurostimulation system. In some aspects, the data indicating the last stimulation level can be stored in a memory of the pulse generator which is retrieved by the patent remote 900 when the patient remote 900 switches from the asleep mode to the awake mode. In other aspects, the stimulation level can be stored in a memory of the circuitry within the patient remote 900 portable housing 902.

The stimulation-increase switch 906 can further have a visible and/or tactile surface or feature shaped to indicate to an operator that the stimulation-increase switch 906 is configured to increase or restore the stimulation level of the pulse generator (e.g., as an upward arrow, as a plus sign, etc.). In some aspects, the stimulation-increase switch 906 can be relatively larger than any stimulation-decrease switch 908 also disposed on the exterior of the portable housing 902.

The control surface 903 can also include a stimulation-decrease switch 908 coupled to control electronics and transmission circuitry disposed within the portable housing 902. Actuation of the stimulation-decrease switch 908 can relay an instruction signal to the pulse generator, where the instruction signal can be selected based on duration of time that the stimulation-decrease switch 908 is actuated. When the stimulation-decrease switch 908 is actuated for the first period of time, the patient remote 902 can send a signal to the pulse generator incrementally decrease the stimulation level of the pulse generator, with the time period for a longer switch actuation threshold time being sufficient to assure that the longer duration switch actuation is clearly intentional, typically being three seconds or more. If the stimulation level of the pulse generator is at the minimum selectable level of therapy, actuation of the stimulation-decrease switch 908 for the first period of time can turn off stimulation by the pulse generator. When the stimulation-decrease switch 908 is actuated for a second period of time, the patient remote 902 can send a signal to the pulse generator to store the status of the current stimulation level in a memory and turn off stimulation by the pulse generator. The second period of time can be three seconds or more. In some aspects, when the pulse generator is instructed to turn off stimulation, the pulse generator can gradually ramp down (as shown in FIG. 8) to a zero stimulation status.

The stimulation-decrease switch 908 can further have a visible and/or tactile surface or feature shaped to indicate to an operator that the stimulation-decrease switch 908 is configured to decrease the stimulation level of the pulse generator or turn off stimulation by the pulse generator (e.g., as a downward arrow, as a minus sign, etc.). In some aspects, the memory in which the stimulation level is stored in the patient remote, or alternately the memory may be stored in the pulse generator. In alternative aspects, the stimulation-increase switch 906 and the stimulation-decrease switch 908 can be relatively equal in size.

The incremental increase or decrease of pulse generator stimulation level by the patient remote 900 can be proportional to an existing or current stimulation level. In many aspects, the incremental increase or decrease of pulse generator stimulation level can be a change of a predetermined degree. The predetermined degree can be a percentage of a stimulation level, a fraction of a stimulation level, a specific or static increment of stimulation level, a proportional increment of stimulation level, a range-dependent increment of stimulation level, a variable increment of stimulation level, or the like. In some embodiments, each incremental change can be five percent (5%), more than five percent (5%), or ten percent (10%) of the existing stimulation level, a maximum stimulation level, or a baseline stimulation level. For example, if a pulse generator is delivering treatment at a stimulation level of 2.0 mA, a single step up increasing the stimulation level can be 0.2 mA (10% of 2.0 mA), thereby increasing stimulation to 2.2 mA. A subsequent step up increasing the stimulation level can be 0.22 mA (10% of 2.2 mA), thereby increasing stimulation to 2.42 mA. Similarly, if a pulse generator is delivering treatment at a stimulation level of 4.0 mA, a single step down decreasing the stimulation level can be 0.4 mA (10% of 4.0 mA), thereby decreasing stimulation to 3.6 mA. In various embodiments, the step size by which the pulse generator stimulation level is changed can be 1% to 25% of the existing stimulation level, or any increment or gradient of a percentage within that range. The number of available treatment levels may be between 3 and 15, typically being between 4 and 10, and often being between 5 and 8.

In some alternative embodiments, for example, if a pulse generator is delivering treatment at a baseline or nominal stimulation level of 3.0 mA, a single step up increasing the stimulation level can be ten percent of the baseline stimulation, 0.3 mA (10% of 3.0 mA), thereby increasing stimulation to 3.3 mA. A subsequent step up increasing the stimulation level can also be based on the baseline stimulation level, that step again being 0.3 mA, thereby increasing stimulation to 3.6 mA. Further within this exemplary embodiment, a single step down decreasing stimulation from a baseline level of 3.0 mA can lower the current stimulation level to 2.7 mA, and a subsequent step down can decrease the current stimulation level to 2.4 mA.

In further alternative embodiments, each step of stimulation level can be based on a percentage of a maximum stimulation level. For example, if a pulse generator has a maximum treatment stimulation level of 4.0 mA, each step of stimulation level change can be ten percent of the maximum stimulation level, 0.4 mA (10% of 4.0 mA). Thus, relative to the maximum stimulation level, a single step down decreasing the stimulation level can be at 3.6 mA, a subsequent step down decreasing the stimulation level can be at 3.2 mA, and so forth.

In other alternative embodiments, the patient remote 900 can operate having an automated proportional stimulation step level increments. For example, when the available stimulation range is within a lower amplitude range, the incremental steps can be smaller than those associated with a higher amplitude range. For example, under conditions where the amplitude range of stimulation level for the patient remote 900 is less than 1.0 milliamp (<1.0 mA), the default increment for a step of simulation level can be 0.05 mA. However, under conditions where the amplitude range of stimulation level for the patient remote 900 is from 1.0 to 3.0 milliamps (1.0-3.0 mA), the default increment for a step of simulation level can be 0.10 mA. Further, under conditions where the amplitude range of stimulation level for the patient remote 900 is greater than 3.0 milliamps (>3.0 mA), the default increment for a step of simulation level can be 0.20 mA. The proportional change in stimulation level step can be varied depending on the amount of treatment required, the number of amplitude ranges, the breadth of amplitude ranges, and/or according to other factors controlling the operation of the patient remote 900. The above described incremental steps can also be applied when determining electrode thresholds during electrode characterization and/or programming.

In some embodiments, the patient remote 900 can be set to incrementally adjust stimulation by a step-size defined by a relationship between a maximum stimulation level ($I_{max}$) and a baseline, also referred to as a nominal or normal stimulation level ($I_n$). For example, the $I_{max}$ and the $I_n$ can be determined and set-up by a physician programming the patient remote 900 via the clinician programmer. The amplitude of $I_{max}$ can be set according to the comfort level of a patient (e.g. stimulation level just below where any pain or discomfort is reported by the patient). Where a difference between $I_{max}$ and $I_n$ is $\Delta I$, the increment step size can be a set proportion or percentage of $\Delta I$, for example steps sizes of ½ $\Delta I$, ⅓$\Delta I$, or ¼ $\Delta I$. In some embodiments, the CP automatically sets such an incremental step size (e.g. ⅓$\Delta I$) with the IPG or EPG, for example during electrode characterization and/or programming. Likewise, patient remote 900 can be programmed with a step-size that corresponds to the step-size used by the CP in programming the IPG or EPG. The amount by which the stimulation levels can be adjusted below the nominal stimulation level (e.g. lower range) can be defined to mirror the incremental range between $I_{max}$ and $I_n$ (e.g. upper range). For example, where the increment step size is defined as ⅓$\Delta I$, the range over which the stimulation level can be incrementally adjusted by the patient remote includes seven stimulation levels, where the nominal or normal stimulation level $I_n$ is in the middle of those seven stimulation levels, incrementing up or down at ⅓$\Delta I$ per step allows for a range of stimulation levels that reaches the maximum stimulation level $I_{max}$ on one end of the available treatment range, and a minimum stimulation level that mirrors $I_{max}$ on the other end of the available treatment range, as shown below:

| $-\Delta I$ | $-⅔\Delta I$ | $-⅓\Delta I$ | $I_n$ | $+⅓\Delta I$ | $+⅔\Delta I$ | $+\Delta I$ |
|---|---|---|---|---|---|---|

(where $+\Delta I$ above $I_n$ is $I_{max}$ and $-\Delta I$ is $I_{min}$).

By programming the patient remote 900 to increment stimulation of a coupled pulse generator by a predetermined degree such as ⅓$\Delta I$, a full range of stimulation levels can be achieved relative to a relationship between $I_{max}$ that matches the comfort level of a patient and the nominal stimulation level corresponding to optimized clinically effective therapy. It is understood that the selection of a stimulation level increment step size by programming the patient remote can allow for setting of a stimulation level increment step to be a specific percentage of a maximum stimulation level, or proportional to a range between the maximum stimulation level and the nominal stimulation level. In some embodiments, the pulse generator is configured to adjust stimulation incrementally according to a step-size, such as described in any of the embodiments described herein, in response to an increase or decrease command received from the patient remote. In one aspect, the command can include the step-size by which the stimulation level is adjusted or the command can invoke an incremental adjustment based on a step-size increment stored on a memory of the pulse generator.

In various embodiments, the patient remote 900 can increase and/or decrease the stimulation level by a predetermined percentage. In some embodiments, the predetermined percentage is a set percentage within a range between 5% and 20%, such as about 10% (+/−2%). In some embodiments, the predetermined percentage is the same for incremental increases and decreases, while in other embodiments, the increase increment differs from that of the decrease increment.

The control surface 903 can include a stimulation-level display 910 embedded in the portable housing 902, and electronically coupled to control electronics and transmission circuitry disposed within the portable housing 902 such that the stimulation-level display 910 can indicate the stimulation level being delivered by the pulse generator to a patient. In some embodiments, the stimulation-level display 910 can include a plurality of lights or light emitting diodes (LEDs) arranged on the control surface, where an illuminated subset of the total number of the plurality of lights or LEDs can indicate the current stimulation level of the pulse generator. In some aspects, the stimulation-level display 910 can include seven (7) white-light LEDs. The stimulation-level display 910 can have the plurality of LEDs arranged in a pattern to reflect increases and decreases to the stimulation level of the pulse generator. In arrangements of the stimulation-level display 910 with seven LEDs as illustrated in FIG. 9, a first LED 910-1 can indicate that the pulse generator is set to deliver a stimulation level at the minimum power selectable via the patient remote 900. In such arrangements of the stimulation-level display 910 with seven LEDs, a second LED 910-2, a third LED 910-3, a fourth LED 910-4, a fifth LED 910-5, and a sixth LED 910-6, can indicate (as read from left to right, optionally with all of the lower-level LEDs remaining illuminated as stimulation level increases) progressively increasing power of stimulation levels selectable via the patient remote 900 that the pulse generator is set to deliver. Also in such arrangements, illumination of a seventh LED 910-7 can indicate (optionally with all other stimulation-level LEDs also being illuminated) that the pulse generator is set to deliver a stimulation level at the maximum power selectable via the patient remote 900. In other aspects the stimulation-level display 910 can include green-light, amber-light, or other colored-light LEDs, which can also provide a relative qualitative indication of the power of each stimulation level of the pulse generator. The LEDs used for the stimulation-level display 910 can be of at least three (3) or four (4) varying sizes to provide a relative qualitative indication of the power of each stimulation level of the pulse generator. In other words, relatively smaller LEDs can be used for the stimulation levels closer or trending toward the minimum power selectable via the patient remote 900 and relatively larger LEDs can be used for the stimulation levels closer or trending toward the maximum power selectable via the patient remote 900.

As noted above, a patient remote 900 can be configured to be used with any appropriate respective pulse generator, such that the patient remote 900 can link with and wirelessly communicate with only a single EPG or IPG, so as to avoid inadvertent and unintentional activation, alteration, or triggering of stimulation of other pulse generators. Accordingly, in implementations of the system, a specific patient remote 900 can be paired with a specific pulse generator (e.g., an IPG, an EPG, or the like) such that the patient remote 900 will only, or at least primarily, operate to interact with the paired pulse generator. The pairing of a patient remote 900 and a specific pulse generator can be established by setting the patient remote 900 and the specific pulse generator to transmit and receive data at the same predetermined wireless or radio frequency. While the clinician programmer can be used to set up or configure a patient remote 900, or establish the paring between a patient remote 900 and a pulse generator, in operation for managing stimulation levels, the patient remote 900 only and/or directly communicates with the pulse generator.

FIGS. 9-1 to 9-7 are schematic illustrations of a patient remote showing an increasing progression of stimulation levels by the stimulation-level display 910 LEDs. As noted above, when a patient remote 900 is turned on by actuation of the activation switch 904, the patient remote can wirelessly interrogate and retrieve the current stimulation level of a pulse generator from the neurostimulation system. The patient remote 900 can indicate to a patient that the patient remote 900 is transitioning from the asleep mode to the awake mode by cycling illumination of the stimulation-level display 910 LEDs. Once the current stimulation level of the pulse generator is retrieved by the patient remote, the stimulation-level display 910 can illuminate a corresponding number of LEDs to indicate to a patient the current stimulation level of the pulse generator. At any given stimulation level, the LED indicating that stimulation level can be illuminated along with all of the LEDs representative of lower stimulation levels. In other aspects, at any given stimulation level, the patient remote 900 can illuminate only the LED indicating that specific stimulation level.

The available stimulation levels of the pulse generator can be programmed relative to a baseline stimulation level, and the patient remote 900 can be configured provide a limited range of selectable stimulation levels either greater than and/or less than the baseline stimulation level, and ideally both. The baseline stimulation level can be selected to correspond to illuminate any one of a plurality of LEDs for the stimulation-level display 910, which can further indicate the number of selectable stimulation levels greater than and less than the baseline stimulation level. In some embodiments, the pulse generator can be programmed to have three selectable stimulation levels greater than the baseline stimulation level and three selectable stimulation levels less than the baseline stimulation level. In such embodiments, when the pulse generator is set to the baseline stimulation level, the fourth LED 910-4 on the patient remote 900 is illuminated (optionally along with first, second, and third LEDs). In other embodiments, the pulse generator can be programmed to have four selectable stimulation levels greater than the baseline stimulation level and two selectable stimulation levels less than the baseline stimulation level. In such embodiments, when the pulse generator is set to the baseline stimulation level, the third LED 910-3 of the patient remote 900 is illuminated (optionally along with first and second LEDs). In alternative aspects, the pulse generator can be programmed such that at the baseline stimulation level, one of the second LED 910-2, the fifth LED 910-5, or the sixth LED 910-6 on the patient remote 900 is illuminated, with corresponding selectable stimulation levels greater than and less than the baseline stimulation level.

Moreover, the baseline stimulation level can be selected to ensure that any adjustment to the therapy via the patient remote remains within a clinically effective range whenever stimulation is applied. In some aspects the clinically effective range of stimulation by the pulse generator can be from about 0.5 mA to about 4 mA. In other aspects, the clinically effective range of stimulation by the pulse generator can be from about 1 mA to about 3 mA. In alternative aspects, the ideal clinically effective range of stimulation by the pulse generator can be from about 0.3 mA to about 2.5 mA, while further for such aspects, stimulation by the pulse generator that is less than 0.3 mA and between from about 2.5 mA to about 4 mA can also be clinically effective at providing treatment. In some embodiments, stimulation is limited to below 4 mA. It is appreciated that the above ranges can be utilized in characterizing and/or programming the neurostimulation device as well. For example, electrodes with stimulation thresholds that provide a desired parameter (e.g. sensory or motor response) an can be categorized as to their suitability for delivering neurostimulation based on which range the threshold lies. For example, in some embodiments, electrodes with a threshold between 0.3-2.5 mA can be considered preferred electrodes for use in neurostimulation therapy delivery, electrodes with thresholds less than 0.3 mA and between 2.5-4 mA can be considered acceptable, and electrodes with thresholds greater than 4 mA can be considered unacceptable for delivering neurostimulation. It is understood that these ranges are an example that is applicable to certain embodiments and certain therapies (e.g. sacral neuromodulation for treatment of OAB and fecal incontinence) and that various other ranges can apply to various other neurostimulation systems and/or therapies.

Accordingly, the baseline stimulation level can be selected to have (1) a pulse amplitude or power within the clinically effective range and (2) a proportional incremental change for increasing or decreasing stimulation relative to the baseline stimulation level such that, at either the maximum or minimum stimulation level selectable via the patient remote, the therapy delivered by the pulse generator remains within the clinically effective range. In further embodiments, the clinically effective range of the pulse generator can include pulses having a pulse amplitude in a range between 0 mA to 1,000 mA, 0 mA to 100 mA, 0 mA to 50 mA, or 0 mA to 25 mA.

In an exemplary embodiment, the pulse generator can be programmed to have a baseline stimulation of 2.0 mA with three selectable stimulation levels greater than the baseline stimulation level and three selectable stimulation levels less than the baseline stimulation level, where each step of adjustment can be ten percent (10%) of the existing or current stimulation level. In such an embodiment, the baseline stimulation level of 2.0 mA is represented in the stimulation-level display 910 by the fourth LED 910-4 being illuminated, the minimum stimulation level selectable by the patient remote 900 is 1.458 mA (represented by the first LED 910-1 being illuminated), and the maximum stimulation level selectable by the patient remote 900 is 2.662 mA (represented by the seventh LED 910-7 being illuminated).

In an alternative exemplary embodiment, the pulse generator can be programmed to have a baseline stimulation of 2.0 mA with four selectable stimulation levels greater than the baseline stimulation level and two selectable stimulation levels less than the baseline stimulation level, where each step of adjustment can be ten percent (10%) of the existing or current stimulation level. In such an embodiment, the baseline stimulation level of 2.0 mA is represented in the stimulation-level display 910 by the third LED 910-3 being illuminated, the minimum stimulation level selectable by the patient remote 900 is 1.62 mA (represented by the first LED 910-1 being illuminated), and the maximum stimulation level selectable by the patient remote 900 is 2.9282 mA (represented by the seventh LED 910-7 being illuminated).

Table 2 set forth below summarizes the functionality resulting from actuation of each of the activation switch 904, the stimulation-increase switch 906, and the stimulation-decrease switch 908, which in some embodiments are in part dependent on the status mode (i.e., awake or asleep) of the patient remote 900. As noted above, when the patient remote 900 is in the asleep mode, both of the stimulation-increase switch 906 and the stimulation-decrease switch 908 are inactive.

light 913g (as represented by the solid-line wavefront illustration). In FIG. 9-9, the therapy-remaining display 912 is shown emitting an amber light 913a (as represented by the broken-line wavefront illustration). In some embodiments, the therapy-remaining display 912 can disposed on the exterior surface of the portable housing 902, such as on the control surface 903. Further, the therapy-remaining display 912 can illuminate with a constant (non-flashing) emission of light, or can illuminate in a flashing or intermittent mode. In implementations of the patient remote 900 where the therapy-remaining display 912 is a bi-color LED, the color of light emitted by the therapy-remaining display 912 and whether the light is emitted as constant or flashing can provide an observer with a qualitative indication of how much therapy and/or battery life is remaining in a neurostimulation system pulse generator.

In an exemplary implementation, the therapy-remaining display 912 can emit a green light 913g when the pulse generator rechargeable battery has at least thirty percent (>30%) of its charge capacity remaining, which can corresponds to at least four (>4) days of nominal stimulation remaining in the neurostimulation system. Further in this implementation, the therapy-remaining display 912 can emit a constant amber light 913a when the pulse generator battery has more than fifteen percent (>15%) but less than thirty percent (<30%) of its charge capacity remaining, which can corresponds to about two to four (2-4) days of nominal stimulation remaining in the neurostimulation system. The therapy-remaining display 912 emitting a constant amber light 913a can be an indication to the patient that the pulse generator battery is relatively low on charge and requires recharging within the subsequent 2-4 days. Further in this implementation, the therapy-remaining display 912 can emit a flashing amber light 913a when the pulse generator battery

TABLE 2

Patient Remote Control Elements and Functionality

| Control Element | Patient Remote Mode | Action | Function |
|---|---|---|---|
| Activation Switch | Asleep | Short actuation | Place Patient Remote in Awake Mode; Communicate with Neurostimulation System; Display Current Stimulation Settings of Neurostimulation System. |
| | Awake | Short actuation | Place Patient Remote in Asleep Mode. |
| Stimulation-Increase Switch | Awake | Short actuation | Increase Stimulation Level UP by One Level; If Neurostimulation System was OFF, Turn Neurostimulation System ON at Stimulation Level 1. |
| | | Long actuation | Turn Neurostimulation System ON and Ramp UP to Stored Previous Stimulation Level. |
| Stimulation-Decrease Switch | Awake | Short actuation | Decrease Stimulation Level DOWN by One Level; If Stimulation Level is Decreased Below Stimulation Level 1, Turn Neurostimulation System OFF. |
| | | Long actuation | Turn Neurostimulation System OFF and Store Previous Stimulation Level. |

FIGS. 9-8 and 9-9 are schematic illustrations of a patient remote 900 with a therapy-remaining display 912 showing levels of therapy remaining for a neurostimulation system. The therapy-remaining display 912 can be an LED indicator capable of emitting one or more colors of light. In FIG. 9-8, the therapy-remaining display 912 is shown emitting a green has less than fifteen percent (<15%) its charge capacity remaining. The therapy-remaining display 912 emitting flashing amber light 913a can be an indication to the patient that the pulse generator battery is critically low on charge, requires immediate recharging, and that the neurostimulation system may automatically turn off. The therapy-remaining display 912 can further indicate that the pulse generator battery is recharging, where in some aspects the therapy-remaining display 912 can emit a flashing green light 913g as the pulse generator battery recharges.

The amount of charge capacity will vary from battery to battery for any pulse generator or neurostimulation system. In some embodiments, the rechargeable battery can have a charge capacity such that 30% of the charge capacity is about 3.55 Volts and 15% of the charge capacity is about 3.45 Volts, where the therapy-remaining display 912 can emit a constant or flashing green light 913g or a constant or flashing amber light 913a as appropriate relative to such voltages.

The amount of therapy remaining for a neurostimulation system and pulse generator is dependent at least on the duration of usage of the neurostimulation system and the level of stimulation the neurostimulation system is instructed to deliver. Accordingly, a processor coupled to the pulse generator can calculate the amount of therapy remaining in a pulse generator based on factors including, but not limited to, the overall capacity of the pulse generator rechargeable battery, the amount of time elapsed since the pulse generator rechargeable battery was last recharged, the average stimulation level at which the pulse generator is operated, the median stimulation level at which the pulse generator is operated, the current voltage of the battery, and the like. In some aspects, the therapy remaining and/or charge capacity of the pulse generator rechargeable battery can be calculated according to one or more of stimulation amplitude, stimulation frequency, stimulation pulse width, stimulation cycling mode (e.g. duty cycle), and impedance. Based on this calculation, when the patient remote 900 interrogates the neurostimulator and retrieves the status of the pulse generator, the therapy-remaining display 912 can illuminate to provide feedback to the patient indicative of the current amount of therapy remaining in the pulse generator.

The visual indicators of the patient remote 900 can be augmented with a haptic or vibratory feedback that punctuates adjustments to stimulation level, where a vibrating element (e.g., a motor, a piezoelectric, etc.) is disposed within the interior of the portable housing 902. The vibrating element can be configured to activate when the pulse generator confirms that an instruction from the patient remote 900 has been received and executed. Such commands from the patient remote can include, but are not limited to, turning on the pulse generator, turning off the pulse generator increasing the stimulation level of the pulse generator, or decreasing the stimulation level of the pulse generator. The vibration element can also be configured to activate for situations including, but not limited to, the patient remote 900 switching from the asleep mode to the awake mode or providing a warning that the rechargeable pulse generator battery has a low charge.

Table 3 set forth below summarizes the feedback indicators provided in embodiments of the patient remote 900, such as the stimulation-level display 910, the therapy-remaining display 912, and the vibration element, and interpretations of the feedback from the indicators.

TABLE 3

Patient Remote Indicators and Feedback

| Indicators | Structure | Patient Remote Status | Feedback |
| --- | --- | --- | --- |
| Stimulation-Level Display | 7 LED array | Remote transition from asleep mode to awake mode. | The LED array displays a "scanning" sequence. |
| | | Remote in awake mode. | A number of LEDs are Illuminated Corresponding to the Current Stimulation Level. |
| Therapy-Remaining Display | Bi-Color LED | Remote in awake mode. | Therapy-Remaining Display Indicates Neurostimulation System Battery Status (e.g., good charge, low charge, very low charge, charging) |
| Haptic | Vibration Motor | Remote in awake mode. | Vibration when the Neurostimulation System Confirms that a Command from the Patient Remote has been Received and Executed. |

The patient remote 900 can further include a fault condition indicator 914, which can illuminate when either or both of the patient remote and the pulse generator are in a fault condition. The fault condition indicator 914 can be an LED, such as a white-light, red-light, or other colored-light LED which can emit a constant or flashing light when either or both of the patient remote and the pulse generator are in a fault condition. Problems with the neurostimulation system that can cause the fault condition indicator 914 to illuminate include, but are not limited to, failure of the pulse generator to respond to commands from the patient remote 900, a low charge for the battery operating the patient remote 900, where fault conditions are of the type common to active implantable devices, which for example may be one or more of low patient remote battery, patient remote software or hardware fault, pulse generator hardware or software fault, and impedance out of range.

In order to make the patient remote 900 a convenient fob device for a patient to carry and used, the portable housing 902 can have a mechanical coupling structure 916 to attach the patient remote 900 with a key ring, karabiner, or other such mounting element. In various aspects, the mechanical coupling structure 916 can be embedded in the structure of the portable housing 902 or looped around a portion of the portable housing 902.

Figures 9, 10:
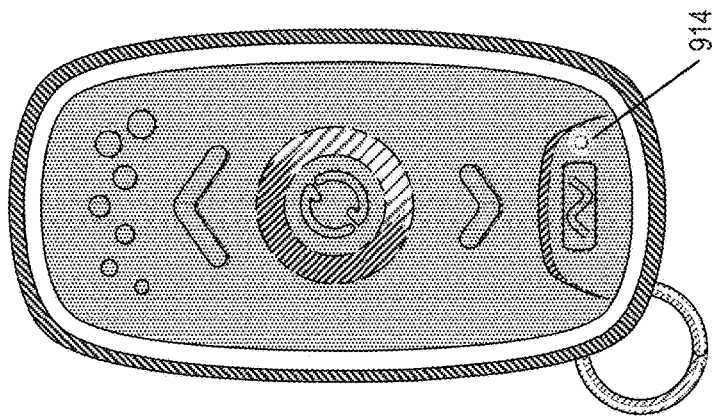
Figure 9:
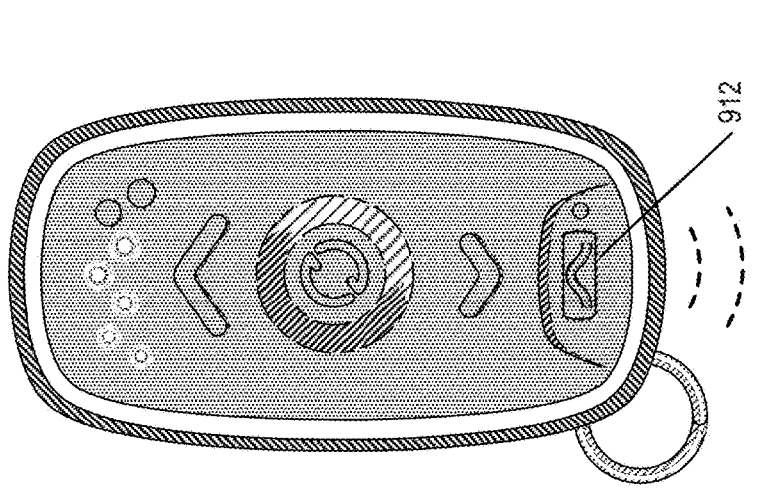
Figures 8, 9:
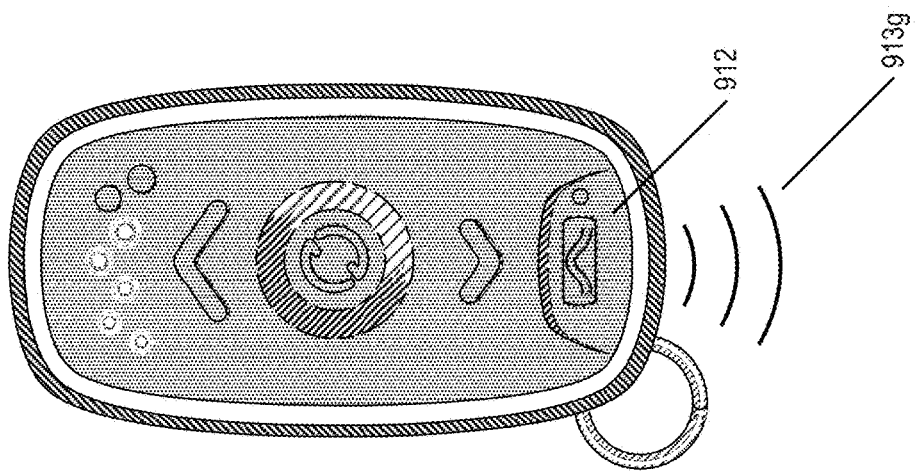
Figure 10:
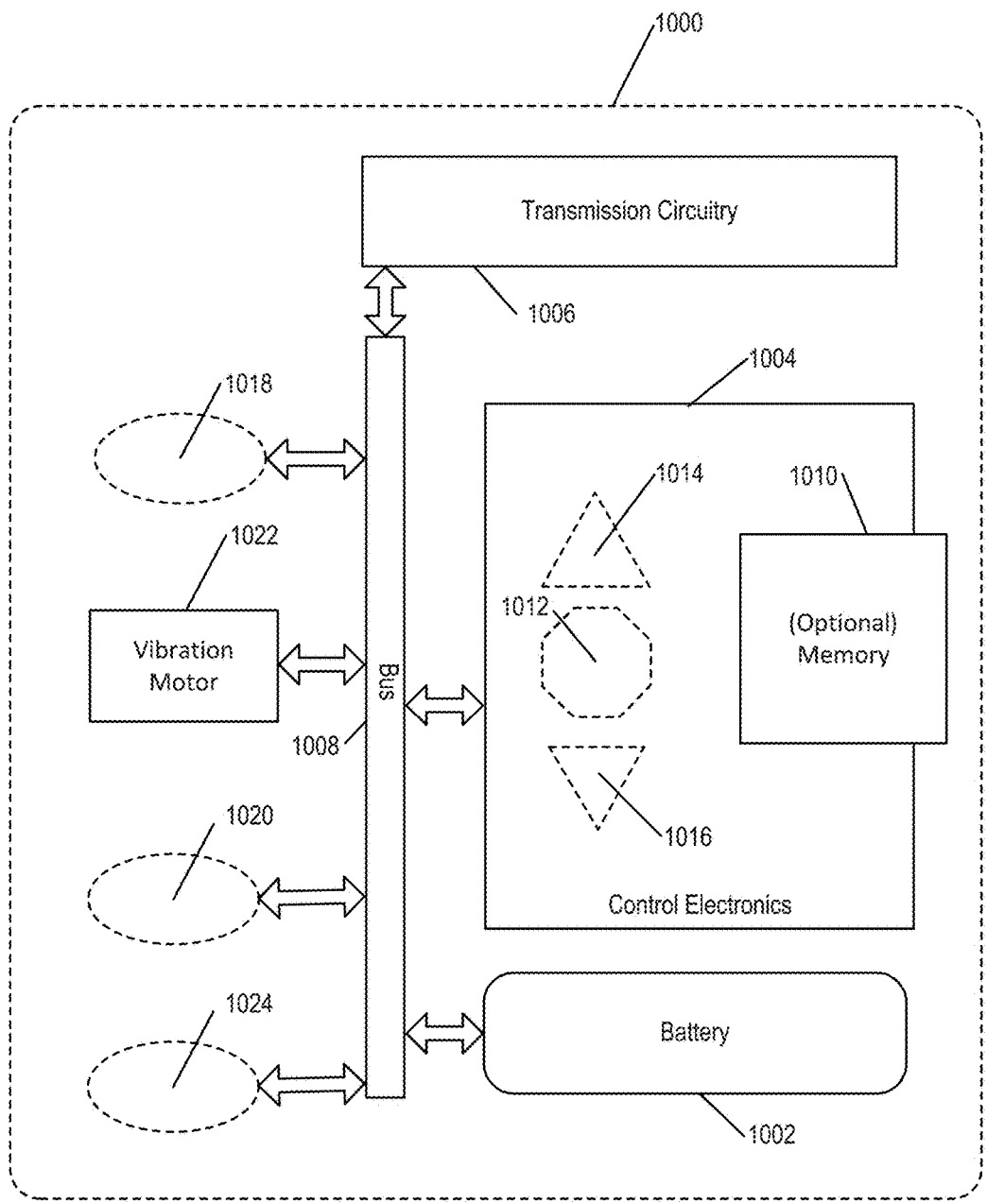

FIG. 10 is a functional block diagram of components of a patient remote 1000. In the embodiment as illustrated, the patient remote 1000 encloses a battery 1002, control electronics 1004, transmission circuitry 1006, and a bus structure 1008 to allow for communication and transmission of power between the components of the patient remote 1000. The patient remote also optionally includes a memory 1010 for storing of data, such as the stimulation status of a linked neurostimulation system. The control electronics 1004 also includes locations where the control electronics 1004 can couple with an activation switch 1012, a stimulation-increase switch 1014, and a stimulation-decrease switch 1016. The bus 1008 can further communicate with a stimulation level display 1018, a therapy-remaining-display 1020, a vibration motor 1022, and a fault condition indicator 1024.

The optional memory 1010 of the patient remote 1000 can store a previous or last stimulation level at which a pulse generator (e.g., an IPG or EPG) paired to the patient remote 1000 was operating. In implementations of the patient remote without an optional memory 1010, the previous or last stimulation level at which a pulse generator paired to the patient remote 1000 was operating can be stored within data memory of the pulse generator, respectively. The status or condition of the pulse generator can be transmitted to the transmission circuitry 1006 of the patient remote 1000 upon interrogation of the pulse generator when the patient remote 1000 is triggered into an awake mode. The status or condition of the pulse generator, particularly the information of the previous or last stimulation level, can be conveyed to the control electronic 1004 of the patient remote to allow for control of the pulse generator via the patient remote based upon the relevant stimulation level of the pulse generator. In many implementations, the transmission of data between a pulse generator and the patient remote can be wireless, and can further be set at a predetermined radio frequency (RF) for a paired set of a patient remote and pulse generator.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A patient remote configured to wirelessly control a nerve-stimulating pulse generator coupled to an implantable lead in a patient, the patient remote comprising:
   a portable housing configured to be operable by a single hand of an operator;
   circuitry disposed within the portable housing, the circuitry configured to wirelessly communicate with the pulse generator;
   an activation button disposed on an exterior surface of the portable housing and coupled to the circuitry, wherein the circuitry is further configured to reconfigure the patient remote between an awake mode and an asleep mode when the activation button is actuated; and
   a stimulation-increase button disposed on the exterior surface of the portable housing, the stimulation-increase button coupled to the circuitry, wherein when the stimulation-increase button is actuated the circuitry is further configured to wirelessly send instruction signals to the pulse generator to increase a stimulation level of the pulse generator;
   wherein when the patient remote is in the awake mode, actuation of the stimulation-increase button for a first period of time causes the circuitry to communicate the instruction signals to the pulse generator to increase the stimulation level of the pulse generator, and actuation of the stimulation-increase button for a second period of time causes the circuitry to communicate the instruction signals to the pulse generator to restore the pulse generator to a last stored stimulation level.

2. The patient remote of claim 1, wherein first period of time comprises a period of time less than a threshold period and the second period of time comprises a period of time greater than the threshold, wherein actuation of the stimulation-increase button for the second period of time ramps the stimulation level to the last stored stimulation level, and wherein the threshold period is three seconds or more.

3. The patient remote of claim 1, further comprising a memory element coupled to the circuitry, and further comprising a stimulation-decrease button disposed on the exterior surface of the portable housing and coupled to the circuitry so as to wirelessly decrease the stimulation level of the pulse generator, wherein when the patient remote is in the awake mode, actuation of the stimulation-decrease button for the first period of time decreases the stimulation level, and actuation of the stimulation-decrease button for the second period of time stores the stimulation level in the memory element for subsequent use as the stored stimulation level and turns off the stimulation by the pulse generator.

4. The patient remote of claim 3, wherein the circuitry is configured so that repeated actuation of the stimulation-increase button can incrementally increase the stimulation level no more than four stimulation levels above a nominal stimulation level and repeated actuation of the stimulation-decrease button can incrementally decrease the stimulation level down respectively no more than three stimulation levels below the nominal stimulation level.

5. The patient remote of claim 3, wherein each stimulation level increase or stimulation level decrease of the pulse generator comprises more than 5 percent of a nominal stimulation level or a current stimulation level.

6. The patient remote of claim 1, further comprising a stimulation-level display disposed on the exterior surface of the portable housing, the stimulation-level display and circuitry configured to indicate a current stimulation level of the pulse generator when the activation button of the patient remote is switched from the asleep mode to the awake mode.

7. The patient remote of claim 6, wherein the stimulation-level display comprises a plurality of light emitting diodes, wherein a number of illuminated light emitting diodes indicates the current stimulation level of the pulse generator.

8. The patient remote of claim 6, wherein the stimulation-level display comprises at least seven light emitting diodes of at least three or four differing sizes, wherein a nominal stimulation level corresponds to illumination of the first three or four light emitting diodes.

9. The patient remote of claim 1, further comprising a therapy-remaining display on the exterior surface of the portable housing, the therapy-remaining display and circuitry configured to indicate therapy remaining status of the pulse generator based on at least a charge or voltage remaining in a battery of the pulse generator and stimulation use by the patient.

10. The patient remote of claim 9, wherein the therapy-remaining display comprises a light emitting diode having a plurality of contrasting display modes, the display modes comprising a plurality of colors or flashing and non-flashing illumination or both and sufficient to indicate if the pulse generator needs re-charging, is charging, or has sufficient charge for at least a threshold number of days of stimulation.

11. The patient remote of claim 10, wherein the therapy-remaining display light emitting diode illuminates with a non-flashing green color to indicate at least 4 days of therapy remaining, illuminates with a non-flashing amber color to indicate 2-4 days of therapy remaining, and illuminates with a flashing amber color to indicate less than 2 days of therapy remaining.

12. The patient remote of claim 1, further comprising an automatic fault condition indicator disposed on the exterior surface of the portable housing configured to provide an alert if the pulse generator is in a fault condition.

13. The patient remote of claim 1, further comprising a haptic indicator coupled to the portable housing and configured to vibrate when a command from the patient remote has been executed by the pulse generator.

14. The patient remote of claim 1, wherein the patient remote is configured to wirelessly control either an external or implantable nerve-stimulating pulse generator and wherein the external or implantable nerve-stimulating pulse generator includes an implantable lead that comprises at least one electrode configured for insertion into a foramen of a sacrum near a sacral nerve.

15. The patient remote of claim 1, wherein the circuitry is configured to send instruction signals such that the stimulation level of the pulse generator is incrementally increased or decreased by a predetermined amount of a maximum stimulation level, a nominal stimulation level, or a current stimulation level of the pulse generator.

16. The patient remote of claim 15, wherein the predetermined amount is a percentage between five and twenty percent of: a maximum stimulation level, a nominal stimulation level, or a current stimulation level of the pulse generator.

17. The patient remote of claim 15, wherein the maximum stimulation level is set according to incremental step-sizes, corresponding to a comfort level of a patient.

18. The patient remote of claim 1, wherein the patient remote maintains the stimulation level after the stimulation level of the pulse generator is set, until the patient remote is operated by the operator to terminate or change stimulation by the pulse generator.

19. The patient remote of claim 1, wherein the patient remote circuitry is configured to pair with and communicate only and/or directly with the pulse generator.

* * * * *